(12) United States Patent
Colau et al.

(10) Patent No.: US 7,790,179 B2
(45) Date of Patent: *Sep. 7, 2010

(54) HOMOGENEOUS ATTENUATED HUMAN ROTAVIRUS POPULATION

(75) Inventors: Brigitte Desiree Alberte Colau, Rixensart (BE); Francoise Denamur, Rixensart (BE); Isabelle Knott, Rixensart (BE); Annick Poliszczak, Rixensart (BE); Georges Thiry, New York City, NY (US); Vincent Vande Velde, New York City, NY (US)

(73) Assignee: GlaxoSmithKline Biologicals, SA, Rixensart (BE)

( * ) Notice: Subject to any disclaimer, the term of this patent is extended or adjusted under 35 U.S.C. 154(b) by 42 days.

This patent is subject to a terminal disclaimer.

(21) Appl. No.: 11/843,256

(22) Filed: Aug. 22, 2007

(65) Prior Publication Data

US 2009/0130145 A1    May 21, 2009

Related U.S. Application Data

(63) Continuation of application No. 10/049,192, filed as application No. PCT/EP00/07695 on Aug. 15, 2000, now Pat. No. 7,285,280.

(30) Foreign Application Priority Data

Aug. 17, 1999  (GB) ................................ 9919468.0
Nov. 18, 1999  (GB) ................................ 9927336.9

(51) Int. Cl.
*A61K 39/00* (2006.01)
*A61K 39/12* (2006.01)
*A61K 39/15* (2006.01)

(52) U.S. Cl. ............... 424/215.1; 424/184.1; 424/204.1
(58) Field of Classification Search ........................ None
See application file for complete search history.

(56) References Cited

U.S. PATENT DOCUMENTS

| | | | |
|---|---|---|---|
| 4,152,421 A | 5/1979 | Tsutsumi et al. |
| 4,341,763 A | 7/1982 | Zygraich |
| 4,571,385 A | 2/1986 | Greenberg et al. |
| 4,624,850 A | 11/1986 | Albert et al. |
| 5,474,773 A | 12/1995 | Ward |
| 5,626,851 A | 5/1997 | Clark et al. |
| 5,773,009 A | 6/1998 | Glass |
| 5,932,223 A | 8/1999 | Burke et al. |
| 6,403,098 B1 | 6/2002 | Burke et al. |
| 6,552,024 B1 | 4/2003 | Chen et al. |
| 2002/0058043 A1 | 5/2002 | Hoshino et al. |

OTHER PUBLICATIONS

Vesikari et al. Safety and immunogenicity of RIX4414 live attenuated human rotavirus vaccine in adults, toddlers and previously uninfected infants. Vaccine 2004, vol. 22, p. 2836-2842.*

Ruiz-Palacios et al. Safety and Efficacy of an Attenuated Vaccine against Severe Rotavirus Gastroenteritis. New England Journal of Medicine 2006, vol. 354, No. 1, p. 11-22.*
Glass et al. The Promise of New Rotavirus Vaccines. New England Journal of Medicine 2006, vol. 354, No. 1, p. 75-77.*
Midthun, et al., "Single Gene Substitution Rotavirus Reassortants Containing the Major Neutralization Protein (VP7) of Human Rotavirus Serotype 4", *Journal of Clinical Microbiology*, 24(5): 822-826 (1986).
Garbag-Chenon, et al., "Reactogenicity and Immunogenicity of Rotavirus WC3 Vaccine in 5-12-Month Old Infants", *Res. Virol.*, 140: 207-217 (1989).
Bernstein, et al., "Safety and Immunogenicity of Live, Attenuated Human Rotavirus Vaccine 89-12", *Vaccine*, 16(4): 381-387 (1998).
Midthun, et al., "Rotavirus Vaccines: An Overview", *Clinical Microbiology Reviews*, 9(3): 423-434 (1996).
Padilla-Noriega, et al., "Human Rotavirus Outer Capsid Protein (VP4) Gene", *Database EMBL 'Online' ROHVP4OCP*, Jul. 4, 1994 (XP002158486).
Crawford, et al., "Human Rotavirus Glycoprotein VP7 mRNA", *Database EMBL 'Online' HRU88717*, Mar. 9, 1997 (XP002158487).
Vesikari, et al., Safety and Immunogenicity of RIX4414 Live Attenuated Human Rotavirus Vaccine in Adults, Toddlers and Previoulsly Uninfected Infants, *Vaccine*, 22:2836-2842 (2004).
Ruiz-Palacios, et al., Safety and Efficacy of an Attenuated Vaccine Against Severe Rotavirus Gastroenteritis, *The New England Journal of Medicine*, 354(1):11-22 (2006).
Glass, et al., "The promise of New Rotavirus Vaccines," *The New England Journal of Medicine*, 354:1, 75-77 (2006).
Glass, et al., "Rotavirus Vaccines: Current Prospects and Future Challenges," *Lancet*, 328(9532):323-332 (2006).
New Drugs and Variations To Existing Drugs [online]. Thearapeutic Goods Administration. Department of Community Services and Health, Australia, Especially p. 6. [retrieved on Jun. 27, 2006]. Retrieved from internet: URL:www.tga.gov.au/docs/pdf/pmrvformg.pdf.
Ward, et al., *J. Clin. Microbiol*, 19:748-753 (1984).
Kirkwood, et al., "Genetic and Antigenic Characterization of a Serotype P[6]G9 Human Rotavirus Strain Isolated in the United States", *Virology*, 256:45-53 (1999).
Pereira, et al., "Genomic Heterogeneity of Simian Rotavirus SA11", *Journal of General Virology*, 65:851-818 (1984).
Vasil'eva, et al., Isolation of the Human Rotavirus in a Cell Culture of Green Money Kidneys, *Voprosy Virusologii*, 3(3):360-362 (1987) Russian. Abstract only provided.
Meng, et al., Physicochemical Stability and Inactivation of Human and Simian Rotaviruses, *Applied and Environmental Microbiology*, 53(4):727-730 (1987).

* cited by examiner

*Primary Examiner*—Zachariah Lucas
*Assistant Examiner*—Louise Humphrey
(74) *Attorney, Agent, or Firm*—Gwynedd Warren; GlaxoSmithKline—Global Patents—US

(57) ABSTRACT

The invention provides an attenuated rotavirus population comprising a single variant or substantially a single variant which is defined by a nucleotide sequence encoding at least one of the major viral proteins designated as VP4 and VP7. The invention particularly provides a rotavirus population designated as P43. The invention further provides a novel formulation for a rotavirus vaccine which is in the form of a quick dissolving tablet for immediate dissolution when placed on the tongue.

16 Claims, 8 Drawing Sheets

FIG 1 VP4 SEQUENCE OF P43 (SEQ ID NO: 1)

```
ATGGCTTCAC TCATTTATAG ACAACTTCTC ACTAATTCAT ATTCAGTAGA   50
TTTACATGAT GAAATAGAGC AAATTGGATC AGAAAAAACT CAGAATGTAA  100
CTATAAATCC GGGTCCATTT GCACAGACTA GATATGCTCC AGTCAATTGG  150
GATCATGGAG AGATAAATGA TTCGACTACA GTAGAACCAA TTTTAGATGG  200
TCCTTATCAG CCAACTACAT TTACTCCACC TAATGATTAT TGGATACTTA  250
TTAATTCAAA TACAAATGGA GTAGTATATG AAAGTACAAA TAATAGTGAC  300
TTTTGGACTG CAGTCGTTGC TATTGAACCG CACGTCAACC CAGTAGATAG  350
ACAATATATG ATATTTGGTG AAAGCAAGCA ATTTAATGTG AGTAACGATT  400
CAAATAAATG GAAGTTTTTA GAAATGTTTA GAAGCAGTAG TCAAAATGAA  450
TTTTATAATA GACGTACATT AACTTCTGAT ACCAGACTTG TAGGAATATT  500
TAAATATGGT GGAAGAGTAT GGACATTTCA TGGTGAAACA CCGAGAGCTA  550
CTACTGACAG TTCAAGTACT GCAAATTTAA ATAATATATC AATTACAATT  600
CATTCAGAAT TTTACATTAT TCCAAGGTCC CAGGAATCTA AATGTAATGA  650
ATATATTAAT AATGGTCTGC CACCAATTCA AAATACTAGA AATGTAGTTC  700
CATTGCCATT ATCATCTAGA TCGATACAGT ATAAGAGAGC ACAAGTTAAT  750
GAAGACATTA TAGTTTCAAA AACTTCATTA TGGAAAGAAA TGCAGTATAA  800
TAGGGATATT ATAATTAGAT TTAAATTTGG TAATAGTATT GTAAAGATGG  850
GAGGACTAGG TTATAAATGG TCTGAAATAT CATATAAGGC AGCAAATTAT  900
CAATATAATT ACTTACGTGA CGGTGAACAA GTAACCGCAC ACACCACTTG  950
TTCAGTAAAT GGAGTGAACA ATTTTAGCTA TAATGGAGGG TTTCTACCCA 1000
CTGATTTTGG TATTTCAAGG TATGAAGTTA TTAAAGAGAA TTCTTATGTA 1050
TATGTAGACT ATTGGGATGA TTCAAAAGCA TTTAGAAATA TGGTATATGT 1100
TAGATCATTA GCAGCTAATT TAAATTCAGT GAAATGTACA GGTGGAAGTT 1150
ATTATTTCAG TATACCAGTA GGTGCATGGC CAGTAATGAA TGGTGGCGCT 1200
GTTTCGTTGC ATTTTGCCGG AGTTACATTA TCCACGCAAT TTACTGATTT 1250
TGTATCATTA AATTCACTAC GATTTAGATT TAGTTTGACA GTTGATGAAC 1300
CACCTTTCTC AATACTGAGA ACACGTACAG TGAATTTGTA TGGATTACCA 1350
GCCGCTAATC CAAATAATGG AAATGAATAC TACGAAATAT CAGGAAGGTT 1400
TTCACTCATT TCTTTAGTTC CAACTAATGA TGATTATCAG ACTCCAATTA 1450
```

FIG. 1

FIG 1 VP4 SEQUENCE OF P43 (SEQ ID NO: 1)

```
TGAATTCAGT GACGGTAAGA CAAGATTTAG AGCGCCAACT TACTGATTTA     1500
CGAGAAGAAT TTAACTCATT GTCACAAGAA ATAGCTATGG CACAAATTGAT    1550
TGATTTAGCA CTGTTGCCTC TAGATATGTT TTCCATGTTT TCAGGAATTA     1600
AAAGTACAAT TGATTTAACT AAATCAATGG CGACTAGTGT AATGAAGAAA     1650
TTTAGAAAAT CAAAATTAGC TACATCAATT TCAGAAATGA CTAATTCATT     1700
GTCAGATGCT GCTTTCATCAG CATCAAGAAA CGTTTCTATT AGATCGAATT    1750
TATCTGCGAT TTCAAATTGG ACTAAATGTTT CAAATGATGT GTCAAACGTA    1800
ACTAATTCAT TGAACGATAT TTCAACACAA ACATCTACAA TTAGTAAGAA     1850
ACTTAGATTA AAAGAAATGA TTACTCAAAC TGAAGGAATG AGCTTTTGACG    1900
ACATTTCAGC AGCTGTACTA AAAACAAAAA TAGATATGTC TACTCAAATT     1950
GGAAAAAATA CTTTACCTGA TATAGTTACA GAAGCATCTG AGAAATTTAT     2000
TCCAAAACGA TCATATCGAA TATTAAAGGA TGATGAAGTA ATGGAAATTA     2050
ATACTGAAGG AAAATTCTTT GCATACAAAA TTAATACATT TGATGAAGTG     2100
CCATTCGATG TAAATAAATT CGCTGAACTA GTAACAGATT CTCCAGTTAT     2150
ATCAGCGATA ATCGATTTTA AGACATTGAA AAATTAAAT GATAATTATG      2200
GAATCACTCG TACAGAAGCG TTAAATTTAA TTAAATCGAA TCCAAATATG     2250
TTACGTAAAATT TCATTAATCA AATAATCCA ATTATAAGGA ATAGAATTGA    2300
ACAGTTAAAATA CTACAATGTA AATTGTGAGA ACGCTATTGA GGATGTGACC   2350
```

FIG. 1 (CON'T)

FIG 2 VP7 SEQUENCE OF P43 (SEQ ID NO: 2)

```
ATGTATGGTC TTGAATATAC CACAATTCTA ATCTTTCTGA TATCAATTAT    50
TCTACTCAAC TATATATTAA AATCAGTAAC TCGAATAATG GACTACATTA   100
TATATAGATC TTTGTTGATT TATGTAGCAT TATTGCCCTT GACAAGAGCT   150
CAGAATTATG GGCTTAACTT ACCAATAACA GGATCAATGG ACACTGTATA   200
CGCTAACTCT ACTCAAGAAG GAATATTTCT AACATCCACA TTATGTTTGT   250
ATTATCCAAC TGAAGCAAGT ACTCAAATTA ATGATGGTGA ATGGAAAGAC   300
TCATTGTCAC AAATGTTTCT CACAAAAGGT TGGCCAACAG GATCAGTCTA   350
TTTTAAAGAG TATTCAAGTA TTGTTTGATTT TTCTGTCGAT CCACAATTAT   400
ATTGTGATTA TAACTTAGTA CTAATGAAAT ATGATCAAAA TCTTGAATTA   450
GATATGTCAG AGTTAGCTGA TTTAATATTG AATGAATGGT TATGTAATCC   500
AATGGATATA ACATTATATT ATTATCAACA ATCGGGAGAA TCAAATAAGT   550
GGATATCAAT GGGATCATCA TGTACTGTGA AAGTGTGTCC ACTGAATACG   600
CAAATGTTAG GAATAGGTTG TCAAACAACA AATGTAGACT CGTTTGAAAT   650
GGTTGCTGAG AATGAGAAAT TAGCTATAGT GGATGTCGTT GATGGGATAA   700
ATCATAAAAT AAATTTGACA ACTACGACAT GTACTATTCG AAATTGTAAG   750
AAGTTAGGTC CAAGAGAGAA TGTAGCTGTA ATACAAGTTG GTGGCTCTAA   800
TGTATTAGAC ATAACAGCAG ATCCAACGAC TAATCCACAA ACTGAGAGAA   850
TGATGAGAGT GAATTGGAAA AAATGGTGGC AAGTATTTTA TACTATAGTA   900
GATTATATTA ACCAAATCGT GCAGGTAATG TCCAAAAGAT CAAGATCATT   950
AAATTCTGCA GCTTTTTATT ATAGAGTATA GATATATCTT AGATTAGATC  1000
GATGTGACC
```

NEUTRALIZATION TITER OF SERA TAKEN FROM P33 VACCINATED INFANTS AGAINST P33 DERIVED ROTAVIRUS CLONES.

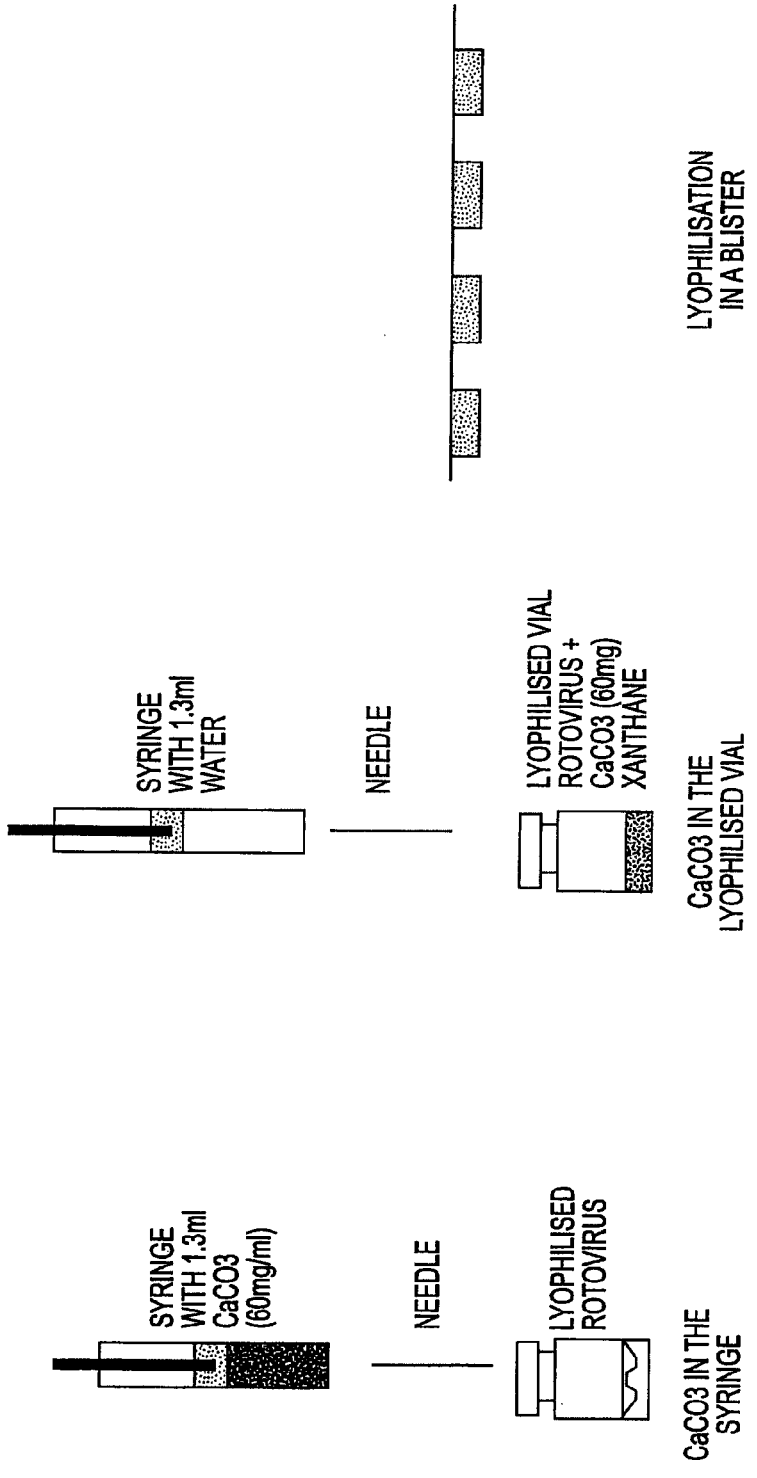

HOMOGENEOUS ATTENUATED HUMAN ROTAVIRUS POPULATION

CROSS-REFERENCE TO RELATED APPLICATIONS

This application is a continuation of U.S. Ser. No. 10/049,192, which is a §371 application of International Application PCT/EP00/07965, filed 15 Aug. 2000, which are incorporated herein by reference. This application also claims benefit of the filing dates of UK Application No. GB 9919468.0, filed 17 Aug. 1999, and UK Application No. GB 9927336.9, filed 18 Dec. 1999.

FIELD OF THE INVENTION

This invention relates to novel vaccine formulations, methods for preparing them and their use in therapy. In particular the present invention relates to novel rotavirus vaccine formulations.

Acute, infectious diarrhea is a leading cause of disease and death in many areas of the world. In developing countries, the impact of diarrheal disease is staggering. For Asia, Africa and Latin America, it has been estimated that there are between 3-4 billion cases of diarrhea each year and of those cases about 5-10 million result in death (Walsh, J. A. et al.: N. Engl. J. Med., 301:967-974 (1979)).

BACKGROUND OF THE INVENTION

Rotaviruses have been recognised as one of the most important causes of severe diarrhea in infants and young children (Estes, M. K. Rotaviruses and Their Replication in Fields Virology, Third Edition, edited by Fields et al., Raven Publishers, Philadelphia, 1996). It is estimated that rotavirus disease is responsible for over one million deaths annually. Rotavirus-induced illness most commonly affects children between 6 and 24 months of age, and the peak prevalence of the disease generally occurs during the cooler months in temperate climates, and year-round in tropical areas. Rotaviruses are typically transmitted from person to person by the faecal-oral route with an incubation period of from about 1 to about 3 days. Unlike infection in the 6-month to 24-month age group, neonates are generally asymptomatic or have only mild disease. In contrast to the severe disease normally encountered in young children, most adults are protected as a result of previous rotavirus infection so most adult infections are mild or asymptomatic (Offit, P. A. et al. Comp. Ther., 8(8):21-26, 1982).

Rotaviruses are generally spherical, and their name is derived from their distinctive outer and inner or double-shelled capsid structure. Typically, the double-shelled capsid structure of a rotavirus surrounds an inner protein shell or core that contains the genome. The genome of a rotavirus is composed of 11 segments of double-stranded RNA which encode at least 11 distinct viral proteins. Two of these viral proteins designated as VP4 and VP7 are arranged on the exterior of the double-shelled capsid structure. The inner capsid of the rotavirus presents one protein, which is the rotavirus protein designated VP6. The relative importance of these three particular rotaviral proteins in eliciting the immune response that follows rotavirus infection is not yet clear. Nevertheless, the VP6 protein determines the group and subgroup antigen, and VP4 and VP7 proteins are the determinants of serotype specificity.

VP7 protein is a 38,000 MW glycoprotein (34,000 MW when non-glycosylated) which is the translational product of genomic segment 7, 8 or 9, depending on the strain. This protein stimulates formation of the major neutralising antibody following rotavirus infection. VP4 protein is a non-glycosylated protein of approximately 88,000 MW which is the translational product of genomic segment 4. This protein also stimulates neutralising antibody following rotavirus infection.

Since VP4 and VP7 proteins are the viral proteins against which neutralising antibodies are directed, they are believed to be prime candidates for development of rotavirus vaccines, affording protection against rotavirus illness.

Natural rotavirus infection during early childhood is known to elicit protective immunity. A live attenuated rotavirus vaccine is thus highly desirable. Preferably this should be an oral vaccine, as this is the natural route of infection of the virus.

Early vaccine development for preventing rotavirus infections began in the 1970s after the discovery of the virus. Initially, attenuated strains from animals and humans were studied and had mixed or disappointing results. More recent efforts have focused on human-animal reassortants that have been more successful.

A rotavirus strain known as 89-12 has been described by Ward; see U.S. Pat. No. 5,474,773 and Bernstein, D. L. et al, Vaccine, 16 (4), 381-387, 1998. The 89-12 strain was isolated from a stool specimen collected from a 14 month-old child with natural rotavirus illness in 1988. According to U.S. Pat. No. 5,474,773 the HRV 89-12 human rotavirus was then culture-adapted by 2 passages in primary African Green Monkey Kidney (AGMK) cells and 4 passages in MA-104 cells as described by Ward in J. Clin. Microbiol., 19, 748-753, 1984. It was then plaque purified 3 times in MA-104 cells (to passage 9) and grown after 2 additional passages in these cells. One additional passage was made (passage 12) for deposition with the ATCC under the accession number ATCC VR 2272. The deposited strain is known as 89-12C2.

The 1998 paper in Vaccine by Bernstein et al is referred to below as the Vaccine (1998) paper. The paper describes the safety and immunogenicity of an orally administered live human rotavirus vaccine candidate. This vaccine was obtained from strain 89-12, attenuated by passaging without plaque purification 26 times in primary AGMK cells and then another 7 times in an established AGMK cell line (33 passages in total).

Hereinafter the aforesaid material which has been serially passaged 26 times will be referred to as P26 and the material which has been serially passaged 33 times will be referred to as P33. In general, rotavirus derived by passaging 89-12 n times will be referred to as Pn.

In the examples which follow the P33 material was passaged a further 5 times on Vero cells. This is referred to as P38.

The P26 and P33 isolates described in the Vaccine (1998) paper were not deposited in a culture collection, nor were they analysed to establish their genetic characterisation.

It has now been found that the P26 population described in the literature comprises a mixture of variants. This has been established by genetic characterisation as described hereinbelow (see examples). P26 is therefore not a reliably consistent population for further passages, in particular for the production of vaccine lots. Similarly, P33 comprises a mixture of variants and is not reliably consistent for the production of vaccine lots.

It has been found that the P26 material is a mixture of at least three VP4 gene variants. P33 and P38 are similarly a mixture of two variants. These variants appear to be antigenically different, in terms of neutralising epitopes, to the 89-12C2 strain deposited at the ATCC when evaluating the neutralizing antibody titers of sera from infants vaccinated with P33 against these variants. This is illustrated in FIG. 3.

Furthermore it has been found that when the P33 material is administered to infants, two identified variants are replicated and excreted. Of 100 vaccinated infants, only 2 showed signs of gastro-enteritis due to rotavirus infection, while 20% of a placebo group were infected. These findings suggest that the identified variants are associated with protection from rotavirus disease. The present invention provides a method of separating rotavirus variants and an improved live attenuated rotavirus vaccine derived from a cloned (homogeneous) human rotavirus strain.

SUMMARY OF THE INVENTION

Accordingly, according to a first aspect the present invention provides an attenuated rotavirus population (isolate), characterised in that it comprises a single variant or substantially a single variant, said variant defined by the nucleotide sequence encoding at least one of the major viral proteins designated as VP4 and VP7.

Preferably the rotavirus population according to the invention is a cloned variant.

By a population comprising a single variant, or substantially a single variant, is meant a rotavirus population which does not contain more than 10%, and preferably less than 5% and most preferably less than 1% of a different variant or variants. Virus populations can be purified to homogeneity or substantial homogeneity by passaging on suitable cell types or by performing a series of one or more cloning steps.

An advantage of the invention is that a population comprising a single variant is more suitable for the formulation of a consistent vaccine lot. Particular variants defined by nucleotide sequences encoding the major viral protein may also be associated with enhanced efficacy in the prevention of rotavirus infection.

In one preferred aspect, the single or substantially single variant in the rotavirus population of the invention is a variant in which the VP4 gene comprises a nucleotide sequence comprising at least one of the following: an adenine base (A) at position 788, an adenine base (A) at position 802 and a thymine base (T) at position 501 from the start codon.

In a further aspect the single or substantially single variant in the population of the invention is a variant in which the VP7 gene comprises a nucleotide sequence comprising at least one of the following: a thymine (T) at position 605, an adenine (A) at position 897, or a guanine (G) at position 897 from the start codon. Preferably at position 897 there is an adenine (A).

In a preferred aspect the single variant in the population according to the invention has an adenine (A) at positions 788 and 802 and a thymine (T) at position 501 from the start codon in the VP4 gene sequence.

In another preferred aspect the single variant in the population according to the invention has a thymine (T) at position 605 and an adenine/guanine (A/G) at position 897 from the start codon in the VP7 sequence. Most preferably in the VP7 sequence there is an adenine (A) at position 897.

In a particularly preferred aspect the single variant in the population according to the invention has an adenine (A) at positions 788 and 802 and a thymine (T) at position 501 from the start codon in the VP4 gene sequence, and a thymine (T) at position 605 and an adenine/guanine (A/G) at position 897 from the start codon in the VP7 sequence. Most preferably in the VP7 sequence there is an adenine (A) at position 897.

In another aspect the single variant comprises a nucleotide sequence encoding a VP4 protein wherein the nucleotide sequence is as shown in FIG. 1 (SEQ ID NO: 1), and/or a nucleotide sequence encoding a VP7 protein wherein the nucleotide sequence is as shown in FIG. 2 (SEQ ID NO: 2).

The present invention also provides a method of producing a rotavirus population comprising a substantially single variant, the method comprising:
 passaging a rotavirus preparation on a suitable cell type;
 optionally selecting homogeneous culture using the steps of either:
 a) limit dilution; or
 b) individual plaque isolation; and
 checking for the presence of a substantially single variant by carrying out a sequence determination of an appropriate region of the VP4 and/or VP7 gene sequence.

The sequence determination may suitably be carried out by a quantitative or semi-quantitative hybridisation technique such as slot blot hybridisation or plaque hybridisation.

Preferably the selected variant is a variant which is replicated and excreted when the starting rotavirus preparation is administered to a human subject, in particular a child.

The resulting cloned virus population resulting from the method according to the invention may be amplified by further passaging on a suitable cell line.

Suitable cell types for passaging the rotavirus population in the above method include African green monkey kidney (AGMK) cells, which may be established cell lines or primary AGMK cells. Suitable AGMK cell lines include for example Vero (ATCC CCL-81), DBS-FRhL-2 (ATCC CL-160), BSC-1 (ECACC 85011422) and CV-1 (ATCC CCL-70). Also suitable are MA-104 (rhesus monkey) and MRC-5 (human—ATCC CCL-171) cell lines. Vero cells are particularly preferred for amplification purposes. Passaging on Vero cells gives a high virus yield.

Techniques for checking whether there is a single variant in a virus population resulting from the method, and for determining the nature of that single variant involve standard sequencing or hybridisation procedures known in the art and are described hereinbelow.

In a preferred aspect the method of the invention is carried out using an appropriate rotavirus, particularly rotavirus having the characteristics of the 89-12 strain or of a passaged derivative thereof.

A particularly preferred single variant population is P43, which was obtained from P33 (an isolated human rotavirus passages 33 times in culture on appropriate cell types) by a series of end dilution cloning steps followed by passaging the cloned material on Vero cells for amplification.

A P43 population was deposited at the European Collection of Animal Cell Cultures (ECACC), Vaccine Research and Production Laboratory, Public Health Laboratory Service, Centre for Applied Microbiology and Research, Porton Down, Salisbury, Wiltshire, SP4 0JG, United Kingdom on 13 Aug. 1999 under the deposition number 99081301, under the terms of the Budapest Treaty.

Although this indicated public availability is the simplest method of obtaining the human rotavirus P43, it is not altogether impossible or improbable that similar and functionally substantially identical rotaviruses might be produced by these or other methods in view of the teachings of this invention. Such functionally substantially identical rotaviruses are considered to be biologically equivalent to the human rotavirus P43 of this invention and therefore are within the general scope of the present invention. It will therefore be understood that the invention encompasses rotavirus populations having the characteristics of the P43 variant as described herein.

It will also be understood that the invention encompasses materials derived from the deposited P43 ECACC 99081301 by subjecting it to further processing such as by propagating it by further passaging, cloning, or other procedures using the live virus or by modifying P43 in any way including by genetic engineering techniques or reassortant techniques. Such steps and techniques are well known in the art.

Materials derived from the deposited P43 which are covered by the invention include protein and genetic material. Of particular interest are reassortant rotaviruses which comprise at least one antigen or at least one segment of P43, for example reassortants which comprise a virulent strain of rotavirus in which one or part of one of the 11 genome segments has been replaced by the genome segment or part thereof of P43. Specifically, a rotavirus reassortant in which the segment or partial segment coding for NSP4 is a P43 segment or partial segment, may have useful properties. Reassortant rotaviruses and techniques for preparing them are well known (Foster, R. H. and Wagstaff, A. J. Tetravalent Rotavirus Vaccine, a review. ADIS drug evaluation, Bio-Drugs, Gev, 9 (2), 155-178, 1998).

Materials of particular interest are progeny of P43 and immunologically active derivatives of P43. Immunologically active derivatives means materials obtained from or with the P43 virus, particularly antigens of the virus, which are capable of eliciting an immune response that is reactive against Rotavirus when injected into a host animal.

In adapting the rotavirus to an appropriate cell line, for example Vero cells, it may be necessary to treat the virus so as to get rid of any potential contaminant such as any adventitious agents that may be present and which would otherwise cause contamination. In the case of ether-sensitive adventitious viruses, this may be done by ether treatment as described hereinbelow. The present invention also relates to inclusion of such ether treatment as an optional step in the overall procedure for obtaining an attenuated live rotavirus or vaccine formulated therewith.

Also within the scope of the invention are admixtures of P43 with other rotavirus variants, for example other cloned variants, or with other viruses in particular other attenuated viruses. Such mixtures are useful in the vaccines of the invention which are described hereinbelow.

The present invention also provides a live attenuated rotavirus vaccine which comprises a substantially single variant population admixed with a suitable adjuvant or a pharmaceutical carrier.

Preferably, the rotavirus vaccine according to the invention is a monovalent rotavirus vaccine containing a single rotavirus strain.

The present invention is particularly advantageous in providing a live rotavirus vaccine in which the live attenuated rotavirus is a human rotavirus and does not cause intussusception.

Suitable pharmaceutical carriers for use in the vaccine according to the invention include those known in the art as being suitable for oral administration, especially to infants. Such carriers include and are not limited to carbohydrates, polyalcohols, amino acids, aluminium hydroxide, magnesium hydroxide, hydroxyapatite, talc, titanium oxide, iron hydroxide, magnesium stearate, carboxymethylcellulose, hydroxypropylmethylcellulose, microcrystalline cellulose, gelatin, vegetal peptone, xanthane, caraghenane, arabic gum, β-cyclodextrin.

The invention also provides a process for preparing a rotavirus vaccine, for example by freeze drying the virus in the presence of suitable stabilisers or admixing the virus according to the invention with a suitable adjuvant or pharmaceutical carrier.

It may also be advantageous to formulate the virus of the invention in lipid-based vehicles such as virosomes or liposomes, in oil in water emulsions or with carrier particles. Alternatively or in addition immunostimulants such as those known in the art for oral vaccines may be included in the formulation. Such immunostimulants include bacterial toxins, particularly cholera toxin (CT) in the form of the holotoxin (entire molecule) or the B chain only (CTB) and the heat labile enterotoxin of *E. coli* (LT). Mutated LTs (mLTs) which are less likely to convert to their active form than the native LT are described in WO 96/06627, WO 93/13202 and U.S. Pat. No. 5,182,109.

Further immunostimulants which may advantageously be included are saponin derivatives such as QS21 and monophosphoryl lipid A, in particular 3-de-O-acylated monophosphoryl lipid A (3D-MPL). Purified saponins as oral adjuvants are described in WO 98/56415. Saponins and monophosphoryl lipid A may be employed separately or in combination (e.g. WO 94/00153) and may be formulated in adjuvant systems together with other agents. 3D-MPL is a well-known adjuvant manufactured by Ribi Immunochem, Montana and its manufacture is described in GB 2122204.

A general discussion of vehicles and adjuvants for oral immunisation can be found in Vaccine Design, The Subunit and Adjuvant Approach, edited by Powell and Newman, Plenum Press, New York, 1995.

BRIEF DESCRIPTION OF THE DRAWINGS

FIG. 1 shows the nucleotide sequence of rotavirus P43 VP4 protein.

FIG. 2 shows the nucleotide sequence of rotavirus P43 VP7 protein.

FIG. 4 shows neutralizing titers of sera from P33 vaccinated infants.

FIG. 7A shows shows a rotavirus vaccine product presentation comprising a syringe containing the Calcium carbonate antacid buffer (in a liquid form), and a vial containing the lyophilised rotavirus strain.

FIG. 7B shows shows a rotavirus vaccine product presentation comprising a syringe containing water and a vial containing the lyophilised rotavirus strain, the calcium carbonate antacid buffer and xanthan.

FIG. 7C shows the lyophilisation, performed directly in a blister, of rotavirus, CaCO3 and Xanthane gum together.

DETAILED DESCRIPTION OF THE INVENTION

The invention also provides a method for vaccinating human subjects, especially infants, by administering to a subject in need thereof an effective amount of a vaccine composition according to the invention. Preferably the live attenuated vaccine is administered by oral administration.

In a preferred aspect the vaccine composition of the invention is formulated with an antacid to minimise inactivation of the vaccine by acid in the stomach. Suitable antacid components include inorganic antacids for example aluminium hydroxide $Al(OH)_3$ and magnesium hydroxide $Mg(OH)_2$. Commercially available antacids which are suitable for use in the invention include Mylanta (trade mark) which contains aluminium hydroxide and magnesium hydroxide. These are insoluble in water and are given in suspension.

Aluminium hydroxide is a particularly preferred component of a vaccine composition according to the invention as it can provide not only an antacid effect but also an adjuvantation effect.

Also suitable for use as antacids in the vaccine of the invention are organic antacids such as organic acid carboxylate salts. A preferred antacid in the vaccine composition of the invention contains an organic acid carboxylate salt, preferably a salt of citric acid such as sodium citrate or potassium citrate.

A particularly preferred antacid that may be used in the vaccine composition of the present invention is the insoluble inorganic salt, calcium carbonate ($CaCO_3$). The calcium carbonate is able to associate with the rotavirus and the rotavirus activity is maintained during the association with the calcium carbonate.

To prevent sedimentation of calcium carbonate during the filling step, viscous agents are preferably present in the formulation.

Possible viscous agents that may be used include pseudoplastic excipients. A pseudoplastic solution is defined as a solution having higher viscosity on standing compared to its viscosity under agitation. Excipients of this type are natural polymers such as arabic gum, adragante gum, agar-agar, alginates, pectines or semi-synthetic polymers for example: carboxymethylcellulose (Tyloses C©), methylcellulose (Methocels A®, Viscotrans MC®, Tylose MH® and MB®), hydroxypropylcellulose (Klucels®), and hydroxypropylmethylcellulose (Methocels E® and K®, Viscotrans MPHC®). In general those pseudoplastic excipients are used together with thixotropic agents. Alternative viscous agents that may be used are pseudoplastic excipients with low flowing capacity. Those polymers, at a sufficient concentration, give rise to a structural fluid arrangement resulting in a high viscosity solution having low flowing capacity on standing. A certain quantity of energy needs to be given to the system to allow flowing and transfer. External energies (agitation) are needed to destroy temporarily the structural fluid arrangement in order to obtain a fluid solution. Examples of such polymers are Carbopols® and xanthane gum.

Thixotropic excipents become a gel structure on standing whilst under agitation they form a fluid solution. Examples of thixotropic excipients are: Veegum® (Magnesium-aluminium silicate) and Avicel RC® (about 89% microcrystalline cellulose and 11% Carboxymethylcellulose Na).

The vaccine composition of the present invention preferably comprises a viscous agent selected from xanthane gum or starch.

Thus the vaccine composition of the present invention is preferably formulated with a combination of calcium carbonate and xanthane gum.

Other components of a composition used in the invention suitably include sugars for example sucrose and/or lactose.

The vaccine composition according to the invention may contain additional components including for example flavourings (particularly for an oral vaccine) and bacteriostatic agents.

Different presentations of the vaccine composition according to the invention are envisaged.

In one preferred embodiment, the vaccine is administered as a liquid formulation. Preferably the liquid formulation is reconstituted prior to administration from at least the following two components:

i) virus component ii) liquid component.

In this embodiment, the virus component and the liquid component are normally present is separate containers, which may conveniently be separate compartments of a single vessel, or separate vessels which can be connected in such a way that the final vaccine composition is reconstituted without exposing it to the air.

Prior to reconstitution, the virus may be in a dry form or a liquid form. Preferably the virus component is lyophilised. Lyophilised virus is more stable than virus in an aqueous solution. The lyophilised virus may be suitably reconstituted using a liquid antacid composition to produce a liquid vaccine formulation. Alternatively the lyophilised virus may be reconstituted with water or aqueous solution, in which case the lyophilised virus composition preferably contains an antacid component.

Preferably, the vaccine formulation comprises a virus component formulated with calcium carbonate and xanthane gum in one compartment or vessel and this is reconstituted with water or aqueous solution present in the second compartment or vessel.

In another preferred embodiment, the vaccine composition is a solid formulation, preferably a lyophilised cake which is suitable for immediate dissolution when placed in the mouth. Lyophilised formulations may conveniently be provided in the form of tablets in a pharmaceutical blister pack.

In another aspect the invention provides a rotavirus vaccine in the form of a quick dissolving tablet for oral administration.

In another aspect the invention provides a composition comprising a live attenuated rotavirus strain, in particular a human rotavirus strain, wherein the composition is a lyophilised solid capable of immediate dissolution when placed in the mouth.

Preferably the quick dissolving tablet according to the invention dissolves in the mouth of the subject sufficiently quickly to prevent swallowing of the undissolved tablet. This approach is particularly advantageous for paediatric rotavirus vaccines.

Preferably the virus is a live attenuated human rotavirus which is formulated with an inorganic antacid such as calcium carbonate and a viscous agent such as xanthane gum.

A further aspect of the present invention is to provide a lyophilised formulation wherein the virus component is any rotavirus strain which is formulated with calcium carbonate and xanthane gum.

Vaccines of the invention may be formulated and administered by known techniques, using a suitable amount of live virus to provide effective protection against rotavirus infection without significant adverse side effects in typical vaccinees. A suitable amount of live virus will normally be between $10^4$ and $10^7$ ffu per dose. A typical dose of vaccine may comprise $10^5$-$10^6$ ffu per dose and may be given in several doses over a period of time, for example in two doses given with a two-month interval. Benefits may however be obtained by having more than 2 doses, for example a 3 or 4 dose regimen, particularly in developing countries. The interval between doses may be more or less than two months long. An optimal amount of live virus for a single dose or for a multiple dose regimen, and optimal timing for the doses, can be ascertained by standard studies involving observation of antibody titres and other responses in subjects.

The vaccine of the invention may also comprise other suitable live viruses for protection against other diseases, for example poliovirus. Alternatively other suitable live virus vaccines for oral administration may be given in a separate dose but on the same occasion as the rotavirus vaccine composition according to the invention.

Figure 3:
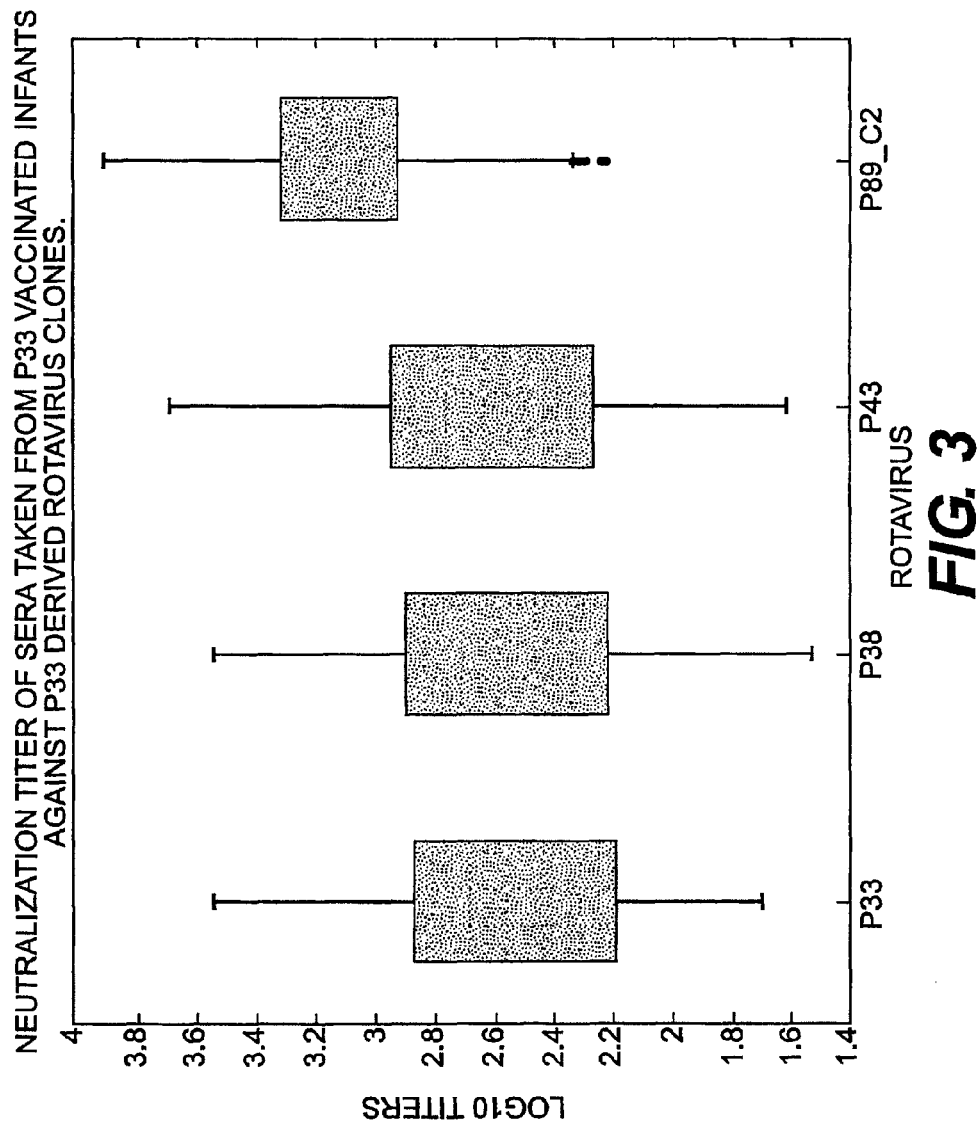
FIG. 3 shows the neutralizing antibody titers of sera from twelve 4 to 6 month old infants vaccinated with P33 against several rotavirus variants P33, P38, P43 and 89-12C2.
Figure 5:
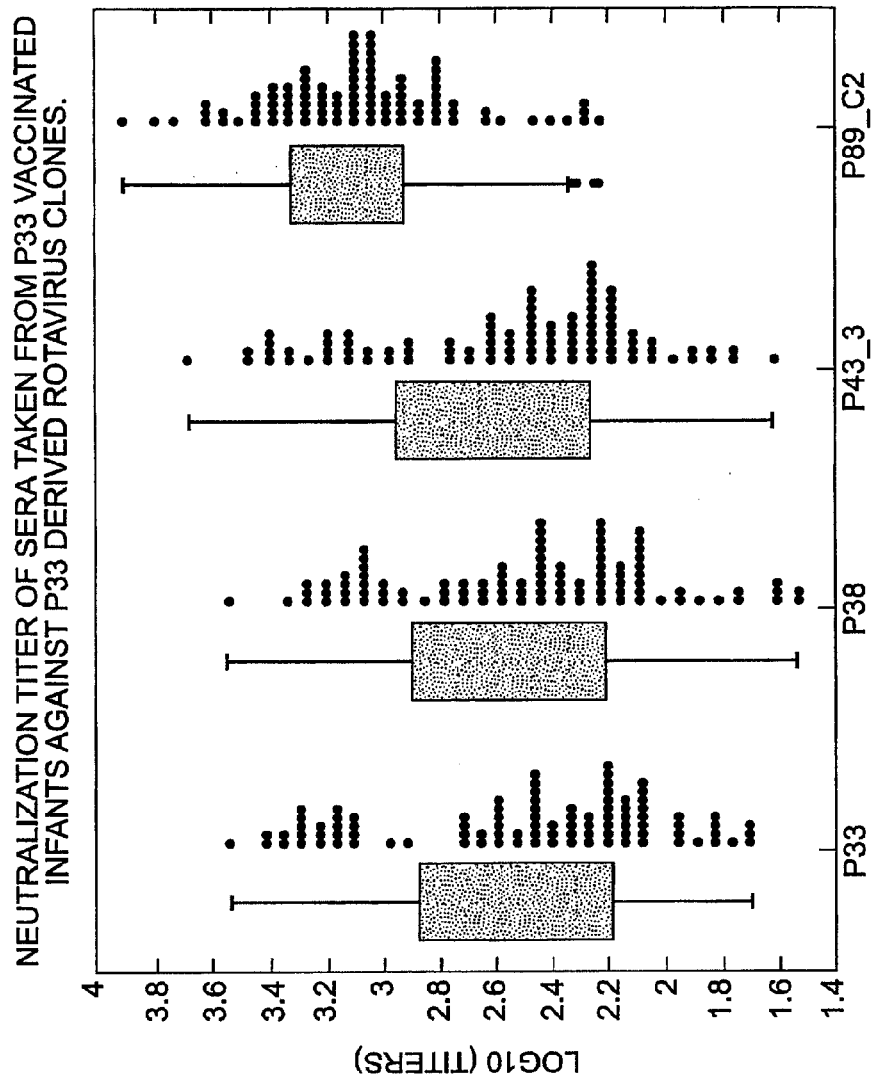
FIG. 5 shows neutralizing titers of sera from P33 vaccinated infants.
Figure 6:
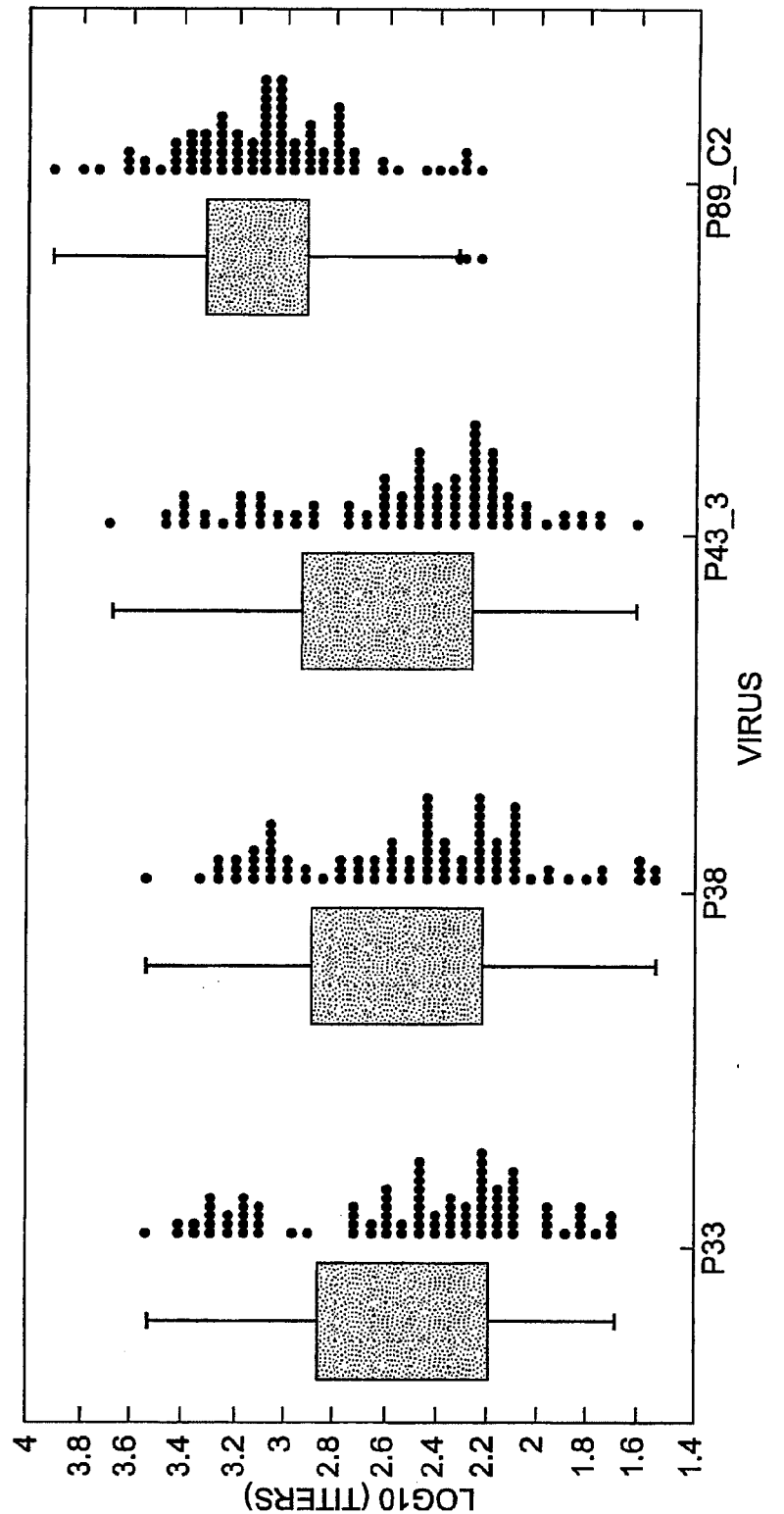
FIG. 6 shows neutralizing titers of sera from P33 vaccinated infants.

Figure Legend for FIG. 3

Sera from twelve 4 to 6 month old infants vaccinated with the P33 material as described in the Vaccine (1998) paper were tested for neutralization of P33, P38, P43 and 89-12C2.

The range of neutralization titers of all the tested sera is similar for P33, P38 and P43. The statistical analysis shows no significant difference in the overall neutralization titers against all three viruses. This suggests that the conformational and non-conformational neutralization epitopes of P33, P38 and P43 are equally well recognized by the anti-P33 sera of P33 vaccinated infants. This observation indirectly suggests that the neutralization epitopes revealed in this in vitro assay were not altered between P33, P38 and P43.

The range of neutralization titers of P89-12C2 however significantly differs from P33, P38 and P43. This observation suggests that the conformational and non-conformational neutralization epitopes of P33, P38 and P43 are not equally well recognized by the anti-P33 sera of P33 vaccinated infants. This observation indirectly suggests that the neutralization epitopes revealed in this in vitro assay were altered between 89-12 C2 and P33, P38 and P43.

The following examples illustrate the invention.

EXAMPLES

Example 1

Demonstration that Strain 89-12 at Passage 26 (P26) is a Mixture of Variants

Sequencing of VP4 and VP7 Genes from Different Passage Lots

Sequencing of VP4 and VP7 genes from passage P26 (primary AGMK cells), passage P33 (established (as opposed to primary) AGMK cell line), passage P41 and passage P43 was performed. Total RNA extraction was reverse transcribed and amplified through PCR in one tube/one step.

Primers Rota 5bis and Rota 29bis amplified the entire VP4 gene and primers Rota 1 and Rota 2bis amplified the entire VP7 gene. The PCR material has been sequenced using different primers (see Table 1).

The passage P26 sequence differed from the passage P33 sequence by 3 bases (at positions 501, 788 and 802 by from the start codon) in VP4 and by three bases in VP7 (108, 605 and 897 by from the start codon).

The passage P26 sequence scans of VP4 and VP7 show at mutated positions the presence of the passage P33 sequence as a background. Thus it can be seen that passage P26 is a mixture of at least 2 variants.

The passage P33 sequence scans seem homogenous in VP4 and heterogeneous for VP7 (see Table 2).

Passage P38 (derived from passage 33) was passaged 5 times on Vero cells and displayed the same set of VP4 and VP7 sequences as passage P33 (AGMK cell line). Thus there was no major change in populations between P33 and P38.

TABLE 1

Oligonucleotides used for RT-PCR and sequencing

| | Name | Sequence | Sequence ID NO: | Position |
|---|---|---|---|---|
| VP7 | Rota 1 | GGC TTT AAA AGA GAG AAT TTC CGT CTG G | (SEQ ID NO:3) | -49 to -22 |
| | Rota 1bis | GGT TAG CTC CTT TTA ATG TAT GGT A | (SEQ ID NO:4) | -16 to 10 |
| | Rota 2bis | GGT CAC ATC GAA CAA TTC TAA TCT AAG | (SEQ ID NO:5) | 1014-988 |
| | Rota 7 | CAA GTA CTC AAA TCA ATG ATG G | (SEQ ID NO:6) | 266-287 |
| | Rota 12 | TGT TGA TTT TTC TGT CGA TCC AC | (SEQ ID NO:7) | 372-394 |
| | Rota 46 | GGT TGC TGA GAA TGA GAA ATT AGC TAT AGT GG | (SEQ ID NO:8) | 651-682 |
| | Rota 18 | CCA CTA TAG CTA ATT TCT CAT TCT CAG CAA CC | (SEQ ID NO:9) | 682-651 |
| VP4 | Rota 5 | TGG CTT CGC CAT TTT ATA GAC A | (SEQ ID NO:10) | 2-23 |
| | Rota 6 | ATT TCG GAC CAT TTA TAA CC | (SEQ ID NO:11) | 878-859 |
| | Rota 5bis | TGG CTT CAC TCA TTT ATA GAC A | (SEQ ID NO:12) | 2-23 |
| | Rota 6bis | ATT TCA GAC CAT TTA TAA CCT AG | (SEQ ID NO:13) | 878-856 |
| | Rota 25 | GGA GTA GTA TAT GAA AGT ACA AAT AAT AG | (SEQ ID NO:14) | 268-296 |
| | Rota 26 | CTA TTA TTT GTA CTT TCA TAT ACT ACT CC | (SEQ ID NO:15) | 296-268 |
| | Rota 27bis | TCG ATA CAG TAT AAG AGA GCA CTT G | (SEQ ID NO:16) | 721-745 |
| | Rota 28 | TTC ATT AAC TTG TGC TCT CTT ATA CTG | (SEQ ID NO:17) | 753-727 |
| | Rota 31 | GTA TAT GTA GAC TAT TGG GAT G | (SEQ ID NO:18) | 1048-1070 |

TABLE 1-continued

Oligonucleotides used for RT-PCR and sequencing

| Name | Sequence | Sequence ID NO: | Position |
|---|---|---|---|
| Rota 32 | CAT CCC AAT AGT CTA CAT ATA C | (SEQ ID NO:19) | 1070-1048 |
| Rota 45 | TGT AAC TCC GGC AAA ATG CAA CG | (SEQ ID NO:20) | 1205-1227 |
| Rota 53 | CGT TGC ATT TTG CCG GAG TTA CA | (SEQ ID NO:21) | 1227-1205 |
| Rota 54 | GTA AGA CAA GAT TTA GAG CGC CA | (SEQ ID NO:22) | 1465-1487 |
| Rota 55 | TGG CGC TCT AAA TCT TGT CTT AC | (SEQ ID NO:23) | 1487-1465 |
| Rota 40 | CTT GAT GCT GAT GAA GCA GCA TCT G | (SEQ ID NO:24) | 1703-1727 |
| Rota 39 | CAG ATG CTG CTT CAT CAG CAT CAA G | (SEQ ID NO:25) | 1727-1703 |
| Rota 33 | CGA TCA TAT CGA ATA TTA AAG GAT G | (SEQ ID NO:26) | 2008-2032 |
| Rota 34 | CAT CCT TTA ATA TTC GAT ATG ATC G | (SEQ ID NO:27) | 2032-2008 |
| Rota 29bis | AGC GTT CAC ACA ATT TAC ATT GTA G | (SEQ ID NO:28) | 2335-2311 |

TABLE 2 oligonucleotides used in hybridization

| Name | Sequence | Sequence ID NO. | Position |
|---|---|---|---|
| VP7 Rota 41 | AGT ATT TTA TAC TAT AGT AGA TTA TAT TAA TC | (SEQ ID NO:29) | 882-913 |
| Rota 42 | AGT ATT TTA TAC TAT GGT AGA TTA TAT TAA TC | (SEQ ID NO:30) | 882-913 |
| VP4 Rota 15 | ATC CCC ATT ATA CTG CAT TCC TTT C | (SEQ ID NO:31) | 807-783 |
| Rota 16 | ATC CCT ATT ATA CTG CAT TTC TTT C | (SEQ ID NO:32) | 807-783 |
| Rota 35 | ATC CCC ATT ATA CTG CAT TTC TTT C | (SEQ ID NO:33) | 807-783 |
| Rota 36 | ATC CCT ATT ATA CTG CAT TCC TTT C | (SEQ ID NO:34) | 807-783 |

The bases shown in bold type in Table 2 are the sites of specific sequence variation in VP4 and VP7.

TABLE 3 sequence variation of VP4 and VP7 genes 3.1

| | VP4 | | | VP7 | | |
|---|---|---|---|---|---|---|
| | 501 bp 167 aa | 788 bp 263 aa | 802 bp 268 aa | 108 bp 36 aa | 605 bp 202 aa | 897 bp 299 aa |
| P26 (AGMK) | A | G/A | G/A | A | C/T | A |
| P33 (AGMK) | T | A | A | G/A | T/C | A/G |
| P38 (VERO) | T | A | A | A/G | T | G/A |
| P43 (VERO) | T | A | A | A | T | A |

N.B. In a second clone from the 3 clones which were developed to the level of production lot, the VP7 897 bp position nucleotide is G, rather than A as in the P43 selected clone. This results in a methionine in place of an isoleucine in the amino acid sequence. Variants corresponding to both the selected P43 clone and the clone in which there is a G in VP7 at 897 bp from the start codon, were excreted in the stools of infants who had been vaccinated with the P33 material.

In Table 3.1, where there are two alternative bases at a particular position, the first of the two represents the base which appears in a major population and the second is the base which appears in a minor population. Major and minor variant populations are judged by the strength of the signal in sequencing.

3.2

| | VP4 | | | VP7 | | |
|---|---|---|---|---|---|---|
| | 501 bp 167 aa | 788 bp 263 aa | 802 bp 268 aa | 108 bp 36 aa | 605 bp 202 aa | 897 bp 299 aa |
| P26 (AGMK) | Leu | Gly/Glu | Gly/Arg | Arg | Thr/Met | Ile |
| P33 (AGMK) | Phe | Glu | Arg | Arg/Arg | Met/Thr | Ile/Met |
| P38 (VERO) | Phe | Glu | Arg | Arg/Arg | Met | Met/Ile |
| P43 (VERO) | Phe | Glu | Arg | Arg | Met | Ile |

Table 3.2 shows the amino acid changes resulting from the nucleotide differences between the variants.

TABLE 4

| | VP4 (788-802 positions) | | | | VP7 (897 position) | |
|---|---|---|---|---|---|---|
| | G-G | A-A | A-G | G-A | A | G |
| Probes | | | | | | |
| Passages | Rota 15 | Rota 16 | Rota 35 | Rota 36 | Rota 41 | Rota 42 |
| P26 | − | + | + | + | nd | nd |
| P33 | − | + | − | − | ++ | + |
| P38 | − | + | − | − | + | ++ |
| P43 | − | + | − | − | + | − |

Slot Blot Hybridization

The change in populations between passages P26 to P33 on AGMK cells has been further confirmed by slot blot hybridization. The VP4 and the VP7 gene fragments generated by RT/PCR were hybridized with oligonucleotide probes specific for each variant (see Table 3.1 and 3.2). In contrast to P26 which hybridized with Rota 16, Rota 35 and Rota 36 and not with Rota 15, the VP4 PCR fragment of the P33 material, at positions 788 and 802 hybridized only with Rota 16 and not with either Rota 15 or Rota 35 or Rota 36. These results established the presence of at least 3 variants in P26 (see Table 4).

For the VP7 PCR fragment of the P33 material, position 897 hybridized with Rota 41 and Rota 42. These results established the presence of at least two variants in the P33 material.

Example 2

Isolation and Characterization of the P43 Clone

To isolate P33 components as a homogeneous virus population, three end-point dilutions of P33/AGMK on Vero cells were performed and the resulting virus was used to infect Vero cells.

Positive wells were selected using two criteria: growth demonstrated by the largest number of foci detected in the wells and the most isolated positive wells on the plates, as is done classically. After 3 end dilution passages in 96 well microtiter plates, 10 positive wells were amplified successively on Vero cells and evaluated for their yield.

Based on yield, three clones were developed to passage level of production lot. Immunorecognition by polyclonal antibodies was shown to be similar both between the three clones and between the clones and P33. Homogeneity of the clones was assessed by slot blot hybridization. The final selection of a single clone was based on yield and sequence.

The selected clone was amplified by successive passages on Vero cells to generate a Master seed, a Working seed and finally production lots.

The selected clone was genetically characterized at different passage levels by sequencing of VP4 and VP7 (identity) and by specific slot blot hybridization of the VP4 and VP7 (homogeneity) of the PCR amplified materials. The sequence of the VP4 and VP7 genes of the P43 material are given in FIGS. 1 (SEQ ID NO:1) and 2 (SEQ ID NO:2) respectively and are identical to P41.

Homogeneity of the selected clone was assessed by a selective hybridization using oligonucleotide probes discriminating nucleotide changes in VP4 and/or VP7 regions for each variant identified during sequencing of P26/primary AGMK (see Table 4).

The VP4 fragment hybridized with Rota 16 and not with Rota 15, Rota 35 or Rota 36.

The VP7 fragment hybridized with Rota 41 and not with Rota 42.

These results confirmed that P43 is a homogeneous population.

Example 3

Removal of Potential Adventitious Virus

Ether was added to P33 (AGMK grown) to a final concentration of 20% for 1 hr. Ether was then bubbled out with $N_2$ for 35 min. No impact on the titre of P33 seed was observed.

Example 4

Formulation of a Live Attenuated Vaccine

The production lots described above are formulated for oral administration to infants by the following method.

1. Lyophilised Virus

Standard techniques are used for preparing virus doses. Frozen purified viral bulk is thawed and diluted with appropriate medium composition, in this case Dulbecco's modified eagle Medium, up to a desired standard viral concentration, in this case $10^{6.2}$ ffu/ml. The diluted virus is then further diluted with lyophilisation stabiliser (sucrose 4%, dextran 8%, sorbitol 6%, amino-acid 4%) up to the target viral titre, in this case $10^{5.6}$ ffu/dose. 0.5 ml aliquots of stabilised virus composition are aseptically transferred to 3 ml vials. Each vial is then partially closed with a rubber stopper, the sample is freeze dried under a vacuum, the vial is then fully closed and an aluminium cap is crimped in place around the vial to keep the stopper in place.

For use, the virus is reconstituted using one of the following antacid reconstituents:

(a) Citrate Reconstituent

Sodium citrate is dissolved in water, sterilized by filtration and aseptically transferred into reconstituent containers in 1.5 ml amounts at a concentration of 544 mg $Na_3Citrate.2H_2O$ per 1.5 ml dose. The reconstituent containers may be for example 3 ml vials, or 4 ml vials, or 2 ml syringes, or soft plastic squeezable capsules for oral administration. As an alternative to maintaining sterile components under sterile conditions, the final container can be autoclaved.

(b) $Al(OH)_3$ Reconstituent

An aseptic aluminium hydroxide suspension (Mylanta—trademark) is aseptically diluted in sterile water, aseptically transferred to reconstituent containers (for example 2 ml syringes, or soft plastic squeezable capsules) in 2 ml amounts each containing 48 mg $Al(OH)_3$. An alternative to using sterile components under sterile conditions is to y irradiate the aluminium hydroxide suspension (preferably at a diluted stage).

Standard ingredients are included to prevent the suspension from settling. Such standard ingredients include for example magnesium stearate, carboxymethylcellulose, hydroxypropylmethylcellulose, microcrystalline cellulose, and silicone polymers. Bacteriostatic agents for example butylparaben, propylparaben or other standard bacteriostatic agents used in food, and flavourings, may also be included.

2. Lyophilised Virus with $Al(OH)_3$ in Liquid Formulation

Standard techniques are used for preparing virus doses. Frozen purified viral bulk is thawed and diluted with appropriate medium composition, in this case Dulbecco's modified eagle Medium, up to a desired standard viral concentration, in this case $10^{6.2}$ ffu/ml. Aluminium hydroxide suspension is added to reach a final quantity of 48 mg/dose and the virus composition is diluted with lyophilisation stabiliser (sucrose 4%, dextran 8%, sorbitol 6%, amino-acid 4%) up to the target viral titre, in this case $10^{5.6}$ ffu/dose. 0.5 ml aliquots of stabilised virus composition are aseptically transferred to 3 ml vials. Lyophilisation and closing of the vials is then carried out as described in part 1.

3. Lyophilised Virus with Al(OH)$_3$ for Blister Presentation

Standard techniques are used for preparing virus doses. Frozen purified viral bulk is thawed and diluted with appropriate medium composition, in this case Dulbecco's modified eagle Medium, up to a desired standard viral concentration, in this case $10^{6.2}$ ffu/ml. Aluminium hydroxide suspension is added to reach a final quantity of 48 mg/dose and the virus composition is diluted with lyophilisation stabiliser which may be sucrose, dextran or amino-acid 4%, or gelatin, or vegetal peptone, or xanthane up to the target viral titre of $10^{5.6}$ ffu/dose. An aseptic filling operation is employed to transfer doses of 0.5 ml or preferably less to blister cavities. The composition is lyophilised, and the blister cavities are sealed by thermic sealing.

Optionally standard ingredients are included to prevent the aluminium hydroxide suspension from settling. Such standard ingredients include for example magnesium stearate, carboxymethylcellulose, hydroxypropylmethylcellulose, microcrystalline cellulose, and silicone polymers. Flavourings may also be included.

Example 5

Rotavirus Viral Titration for Various Formulations

5.1: Comparison between lactose and sucrose based formulations:

| Batch n° | Fomulation composition | Viral titer before lyophilisation | Viral titer after lyophilisation and 1 week at 37° C. |
|---|---|---|---|
| 98G06/01 | Lactose: 2%; Dextran: 4%; Sorbitol: 3%; Amino Acids: 2% | $10^{5.22}$ | $10^{4.67}$ |
| 98G06/03 | Sucrose: 2%; Dextran: 4%; Sorbitol: 3%; Amino Acids: 2% | $10^{5.28}$ | $10^{4.92}$ |

P43 rotavirus was formulated either with sucrose or with lactose as shown in the table above. Viral titration before lyophilisation is the viral titre in the completed formulated liquid (containing sucrose dextran sorbitol aminoacids) and without the lyophilisation step.

Good results are those in which a <0.5 log decrease at the lyophilisation step and <0.5 log decrease during the "1 week at 37° C." (accelerated stability test) are achieved.

The precision of the viral titration is around + or −0.2 log.

The results indicate that sucrose may be used instead of lactose.

5.2: Effect of arginine and replacement of sorbitol by maltitol:

| Batch n° | Fomulation composition | Viral titer at time = zero after lyophilisation | Viral titer after lyopjhilisation and 1 week at 37° C. |
|---|---|---|---|
| 98L16/01 | Lactose: 2%; Dextran: 4%; Sorbitol: 3%; Amino Acids: 2% | $10^{4.8}$ | $10^{4.8}$ |
| 98L16/02 | Lactose: 2%; Dextran: 4%; Sorbitol: 3%; Amino Acids: 2% Arginine: 3% | $10^{4.8}$ | $10^{4.9}$ |
| 98L16/04 | Lactose: 2%; Dextran: 4%; Maltitol: 3%; Amino Acids: 2% Arginine: 3% | $10^{4.7}$ | $10^{5}$ |

The results demonstrate that the addition of arginine (which is known to improve the stability of the virus during lyophilisation and also provides a basic medium in order to compensate for the stomach acidity) maintains the viral titer.

Sorbitol tends to decrease the glass transition temperature of the lyophilised cake by too great a degree. This can be overcome by using maltitol instead of sorbitol as shown above and the viral titer is still maintained.

5.3: Various formulation compositions
This experiment demonstrates that a number of formulations are possible.

| Batch n° | Fomulation composition | Viral titer before lyophilisation | Viral titer after lyophilisation and 1 week at 37° |
|---|---|---|---|
| 99C11/01 | Sucrose: 2%; Dextran: 4%; Sorbitol: 3%; Amino Acids: 2% | $10^{5.24}$ | $10^{5.07}$ |
| 99C11/02 | Sucrose: 2%; Dextran: 4%; Maltitol: 3%; Amino Acids: 2% | $10^{5.09}$ | $10^{4.92}$ |
| 99C11/04 | Dextran: 4%; Maltitol: 3%; Amino Acids: 2% | $10^{4.89}$ | $10^{5.06}$ |

| Batch n° | Fomulation composition | Viral titer at time = zero after lyophilisation | Viral titer after lyophilisation and 1 week at 37° |
|---|---|---|---|
| 99C17/01 | Sucrose: 2%; Dextran: 4%; Sorbitol: 3%; Amino Acids: 2% | $10^{5.40}$ | $10^{5.41}$ |
| 99C17/02 | Sucrose: 2%; Dextran: 4%; Sorbitol: 1.5%; Amino Acids: 2% | $10^{5.30}$ | $10^{4.93}$ |
| 99C17/03 | Sucrose: 2%; Dextran: 4%; Amino Acids: 2% | $10^{5.31}$ | $10^{5.24}$ |
| 99C17/04 | Sucrose: 2%; Dextran: 4%; Maltitol: 3%; Amino Acids: 2% | $10^{4.42}$ | $10^{4.45}$ |

-continued

| Batch n° | Fomulation composition | Viral titer at time = zero after lyophilisation | Viral titer after lyophilisation and 1 week at 37° |
|---|---|---|---|
| 99C17/05 | Sucrose: 2%; Dextran: 4%; Maltitol: 1.5%; Amino Acids: 2% | $10^{4.39}$ | $10^{4.40}$ |
| 99C17/06 | Sucrose: 2%; Dextran: 4%; Sorbitol: 3%; | $10^{5.44}$ | $10^{4.97}$ |
| 99C17/07 | Sucrose: 2%; Dextran: 4%; Sorbitol: 1.5%; | $10^{5.11}$ | $10^{4.89}$ |

5.4: Association between Rotavirus and Al(OH)$_3$ antacid:

| Rotavirus | Al(OH)$_3$ | H$_2$O | Contact time at room temperature | Centrifugation | Supernatant viral titer in ffu/ml | Pellets viral titer in ffu/ml |
|---|---|---|---|---|---|---|
| $10^{5.6}$ ffu/ml | 48 mg in 0.240 ml | 0.76 ml | 30 min | 8000 rpm, 10 min | $10^{3.66}$ | |
| $10^{5.6}$ ffu/ml | 0.48 mg in 0.240 ml | 0.76 ml | 30 min | 8000 rpm, 10 min | $10^{4.41}$ | |
| $10^{5.6}$ ffu/ml | | 1 ml | 30 min | 8000 rpm, 10 min | $10^{5.68}$ | |
| Rotavirus in Lyophilised Cake | 12 mg in 0.120 ml | 1.380 ml | 30 min | 8000 rpm, 10 min | Below detection | $10^{4.7}$ |

Al(OH)$_3$ is used as an antacid. This shows that Rotavirus is associated with the insoluble inorganic salt (Al(OH)$_3$) since it centrifuged together with the Al(OH)$_3$ (decrease of viral activity in the supernatant).

5.5: Dissolution of Al(OH)$_3$ antacid by SodiumCitrate before viral titration

| Viral samples | Dissolution | Conditions | Viral titers ffu/ml |
|---|---|---|---|
| 99B10/06 liquid formulation before lyophilisation; $10^{5.43}$ | 1.5 ml Na$_3$ Citrate | 24 h at room temperature | $10^{5.11}$ |
| 99B10/06: lyophilized $10^{5.43}$ | 1.5 ml Na$_3$ Citrate | 24 h at room temperature | $10^{4.53}$ |

When Rotavirus is associated with the Al(OH)$_3$, it is possible to lyophilise everything (including the Al(OH)$_3$). After lyophilisation, it is possible to recover the Rotavirus by dissolving Al(OH)$_3$ in SodiumCitrate. This step does not damage the Rotavirus and retains its activity after this dissolution step.

5.6: Infectivity of Rotavirus after Liberation of the Al(OH)$_3$-Rotavirus Association:

The mechanism of virus liberation (by dissolution of the carrier) may very well occur in vivo. Indeed below pH 6, aluminium hydroxide becomes completely soluble, and thus, Rotavirus will be liberated in the stomach.

$$Al(OH)_3 + 3H^+ \rightarrow Al^{+++}(\text{water soluble}) + 3H_2O$$

In the stomach, Al$^{+++}$ ions are not absorbed (J. J. Powell, R. Jugdaohsingh and R. P. H. Thompson, *The regulation of mineral adsorption in the gastrointestinal track*, Proceedings of the Nutrition Society (1999), 58, 147-153).

In the intestine, due to the increase of pH, insoluble forms of aluminium are precipitated (Al(OH)$_3$ or AlPO$_4$), and eliminated by the natural way.

It is unknown whether the newly formed Al(OH)$_3$ (or AlPO$_4$) precipitate will be able to re-associate with free Rotavirus. This raises the question of the infectivity of the Al(OH)$_3$-Rotavirus association itself.

Liberation of Rotavirus from the Al(OH)$_3$-Rotavirus association by other mechanisms is also possible. Lysine, for example, interferes with the viral adsorption on Al(OH)$_3$.

Other anions like borate, sulfate, carbonate and phosphate are known to be specifically adsorbed on aluminium hydroxide, thus, theoretically, it should be possible to displace (by competition for the adsorption site) Rotavirus from the Al(OH)$_3$-Rotavirus association.

DRVC003A46
+
12 mg Al(OH)3 in 0.120 ml
+
65 mg Lysine 1.380 ml H2O
+
30 min Room T.
+
Centrifugation 8000 rpm 10 min Culot      Supernatant
+      3.8
dissolution in Citrate below detection Thus, Rotavirus may be liberated from the Rotavirus-Al(OH)$_3$ association and the liberated Rotavirus remains active.

This liberation can be done either by dissolving Al(OH)$_3$ (by HCl in the stomach, or by Na$_3$Citrate in vitro) or by displacing Rotavirus by a basic amino acid (lysine).

5.7: Infectivity of the Al(OH)$_3$-Rotavirus Association

A single dose of lyophilised Rotavirus was reconstituted with water and divided into two parts. The first part, considered as the reference, received an additional volume of water. The second part received 24 mg of $Al(OH)_3$ suspended in 0.240 ml of water (Preclinical viral titrations).

```
        DRVC003A4
            6
            +
         1.5 ml H2O
         /        \
   0.750 ml      0.750 ml
       +             +
   0.240 ml       24 mg
     H2O         Al(OH)3
    1 hour      in 0.240 ml
     5.55         1 hour
                   6.22
```

When $Al(OH)_3$ is present, Rotavirus is active and the viral titration value is higher compared to the reference sample.

This experiment was repeated without dividing the lyophilised dose, and by adding 12 mg $Al(OH)_3$ or 24 mg $Al(OH)_3$.

Here the reference sample was the one reconstituted with a Citrate-Bicarbonate buffer. Thus, the viral titer is again higher in the presence of $Al(OH)_3$.

| DRVC003A46 + 1.5 ml WL buffer | DRVC003A46 + 12 mg Al(OH)3 in 0.120 ml + 1.380 ml H2O | DRVC003A46 + 24 mg Al(OH)3 in 0.240 ml + 1.260 ml H2O |
|---|---|---|
| 5.34 | 6.24 | 6.05 |
| 5.32 | 5.95 | 6.26 |

As in the example above, Rotavirus associates with the $Al(OH)_3$ particles, since the virus can be discarded by centrifugation. DRVC003A46 is a lyophilised formulated Rotavirus (Sucrose: 2%; Dextran: 4%, Sorbitol: 3%; Amino-acids: 2%).

DRVC003A46
+
12 mg Al(OH)3
in 0.120 ml
+
1.380 ml H2O
+
Centrifugation
8000 rpm 10 min Culot
+
1.5 ml
SDSAA
5.78
5.96

Supernatant
<1.44
<1.44

DRVC003A46
+
24 mg Al(OH)3
in 0.240 ml
+
1.260 ml H2O
+

-continued

Centrifugation
8000 rpm 10 min

Culot
+
1.5 ml
SDSAA
5.92
6.11

Supernatant
<1.44
<1.44

SDSAA=Sucrose 2%, Dextran 4%, Sorbitol 3%, Amino-Acid 2%.

According to the viral titration carried out on the supernatant, the quantity of $Al(OH)_3$ needed to adsorb Rotavirus seems to be low (starting with one lyophilised dose 5.7 log) scaling Up viral titration):

| Al(OH)3 | Adsorption time | Titer in supernatant |
|---|---|---|
| 12 mg | 1 hour RT | 2.7 |
| 24 mg | 1 hour RT | 3.4 |
| 48 mg | 1 hour RT | 3.4 |
| 72 mg | 1 hour RT | 2.0 |
| 96 mg | 1 hour RT | Below detection |
| 12 mg | Overnight | 2.7 |
| 24 mg | Overnight | Below detection |
| 48 mg | Overnight | 2.5 |
| 12 mg | Immediate | Below detection |
| 24 mg | Immediate | 2.0 |
| 48 mg | Immediate | Below detection |

Time needed to adsorb Rotavirus on $Al(OH)_3$ seems to be short:

One dose of lyophilised Rotavirus was reconstituted in presence of 24 mg $Al(OH)_3$, and centrifuged after 0, 15, 60 min and 24 hours. The "culot" were resuspended in SDSAA before viral titration:

| Time | Culot | Supernatant |
|---|---|---|
| 0 min | 5.26 | 3.17 |
| 15 min | 5.34 | <1.44 |
| 60 min | 5.96 | <1.44 |
| 24 hours | 6.13 | <1.44 |

5.8: Using $CaCO_3$ as Antacid

In order to avoid aluminium in the vaccine, the antacid $Al(OH)_3$ was replaced by another insoluble inorganic salt: $CaCO_3$ (calcium carbonate).

The phenomena observed with $CaCO_3$ are parallel to those described for $Al(OH)_3$:

Association of Rotavirus with the inorganic salt;

Maintainance of Rotavirus activity when associated with the inorganic salt;

Possibility of liberation of Rotavirus from the association by dissolution of the inorganic base by an acid;

Possibility of co-lyophilisation of the antacid and the Rotavirus.

CaCO₃ and Rotavirus Association

In a first trial, lyophilised Rotavirus (viral titer 5.7) was reconstituted with a suspension of CaCO₃ in water (50 mg in 1.5 ml); and then centrifuged, and the viral titer of the supernatant compared to the culot.

```
        DRVC003A46
             +
        50mg CaCO3
            in
         1.5 ml H2O
             +
       Centrifugation
       8000 rpm 10
            min
          /     \
      Culot    Supernatant
        +        4.46
      1.5 ml
      SDSA
        A
       5.83
        DRVC003A46
             +
        50mg CaCO3
            in
         1.5 ml H2O
             +
       Centrifugation
       8000 rpm 10
            min
          /     \
      Culot    Supernatant
        +        4.33
      1.5 ml
       Na
     Citrate
       5.88
```

This indicates that more that 90% of the Rotavirus is associated with CaCO₃.

Also, when the virus was associated, it was possible to realise the titration and to recover the original viral quantities.

Also, viral titers are slightly higher that those obtained without CaCO₃.

```
        DRVC003A46
             +

1.5 ml H2O
             +

Centrifugation
       8000 rpm 10 min
          /     \
      "Culot"  Supernatant
       4.99      5.03
        DRVC003A46
             +
```

```
        1.5 ml
       W.L Buffer
           |
           ↓
          5.35
```

Quantity of CaCO₃ and Rotavirus Association

Lyophilised Rotavirus was reconstituted with a CaCO₃ suspension in water (1.5 ml):
- 10 mg
- 50 mg
- 100 mg and then centrifuged, and the viral titer of the supernatant compared to the culot.

|  | Extempo + Centri. | | 1 Hour + Centri | |
|---|---|---|---|---|
| CaCO3 | Culots | Surpernatant | Culots | Surpernatant |
| 100 mg | 4.57 | 3.01 | 4.79 | 3.09 |
| 50 mg | 4.17 | 4.15 | 4.22 | 3.86 |
| 10 mg | 3.17 | 4.77 | 3.87 | 4.87 |

Thus, clearly, more CaCO₃ and more virus is associated, and less is found in the supernatant. However, the full dose is not completely recovered (expected a total of 5.3 at least or even 5.8 as obtained earlier—see above).

CaCO₃ Protection of Rotavirus during Baby Rossett-Rice Antacid Titration

Using 10 doses of lyophilised Rotavirus (DRVC003A46) and 50 mg of CaCO₃, two types of baby Rossett-Rice titration were carried out:

In a classic Rossett-Rice titration, the antacid is mixed with Rotavirus and HCl is poured into this medium.

In the "inverse" baby Rossett-Rice, the situation is the reverse: antacid is dropped into the HCl pool (as it occurs in vivo).

| Classical baby Rossett-Rice titration | | | |
|---|---|---|---|
| Lyophi. Rota stored at: | Buffer | Theoretical Viral Titer | Measured Viral Titer |
| 4° C. | 60 mg CaCO3 | 5.3 | 4.6 |
| −80° C. | 60 mg CaCO3 | 5.3 | 4.6 |
| 4° C. | 24 mg Al(OH)3 | 5.4 | <2.9 |
| −80° C. | 24 mg Al(OH)3 | 5.4 | <2.9 |

| Inverse baby Rossett-Rice titration | | | |
|---|---|---|---|
| Lyophi. Rota stored at: | Buffer | Theoretical Viral Titer | Measured Viral Titer |
| 4° C. | 60 mg CaCO3 | 5.3 | 4.6 |
| −80° C. | 60 mg CaCO3 | 5.3 | 4.6 |
| 4° C. | 24 mg Al(OH)3 | 5.4 | <2.9 |
| −80° C. | 24 mg Al(OH)3 | 5.4 | <2.9 |

Thus, in this in vitro experiment, calcium carbonate is able to protect about 20% of Rotavirus from the presence of HCl, while aluminium hydroxide is not able to.

5.9: Lyophilisation of Rotavirus in Presence of CaCO₃ Antacid:

| Batch n° | Composition | Viral titer at time = zero after lyophilisation | Viral titer after lyopjhilisation and 1 week at 37° C. |
|---|---|---|---|
| 99K08/01 | Sucrose: 2%<br>Dextran: 4%<br>Sorbitol: 3%<br>Am. Acids: 2%<br>CaCO₃: 50 mg | $10^{5.28}$ | $10^{5.10}$ |
| 99K08/02 | Sucrose: 2%<br>Dextran: 4%<br>Sorbitol: 3%<br>Am. Acids: 2%<br>CaCO₃: 60 mg | $10^{5.16}$ | $10^{5.15}$ |
| 00C24/01 | Sucrose: 2%<br>Dextran: 4%<br>Sorbitol: 3%<br>Am. Acids: 2%<br>CaCO₃: 60 mg<br>Xanthane 0.3% | $10^{5.07}$ | $10^{4.69}$ |
| 00C24/03 | Sucrose: 2%<br>Dextran: 4%<br>Sorbitol: 3%<br>Am. Acids: 2%<br>CaCO₃: 60 mg<br>Xanthane 0.3% | $10^{5.07}$ | $10^{4.85}$ |
| 00E09/25 | Sucrose: 2%<br>Dextran: 4%<br>Sorbitol: 3%<br>Am. Acids: 2%<br>CaCO₃: 60 mg<br>Xanthane 0.25% | $10^{5.03}$ | $10^{4.91}$ |
| 00E09/30 | Sucrose: 2%<br>Dextran: 4%<br>Sorbitol: 3%<br>Am. Acids: 2%<br>CaCO₃: 60 mg<br>Xanthane 0.30% | $10^{5.01}$ | $10^{4.87}$ |
| 00F26/06 | Sucrose: 2%<br>Dextran: 4%<br>Sorbitol: 3%<br>Am. Acids: 2%<br>CaCO₃: 60 mg<br>Starch: 2% | $10^{4.50}$ | $10^{4.70}$ |

This is the "all in one"—lyophilisation of Rotavirus and antacid (CaCO₃) together in the same vial. To prevent sedimentation of CaCO₃ during the filling step, viscous agents are needed. Examples of such viscous agents include Xanthane gum and Starch. The Rotavirus activity is maintained even in the presence of Xanthane gum and Starch.

5.10 Lyophilised Tablets for Quick Disintegration when placed in the Mouth:

The following formulations demonstrate the "lyoc" concept. That is, quick dissolution of the lyophilised cake in the mouth.

| Batch n° | Fomulation composition | Viral titer before lyophilisation | Viral titer after lyopjhilisation and 1 week at 37° |
|---|---|---|---|
| 99B10/06 | Sucrose 4%<br>Sodium glutamate 3.7%<br>Al(OH)3 48 mg | $10^{5.11}$ | $10^{4.53}$ |
| 99C11/12 | Maltitol 3%<br>Al(OH) 48 mg<br>Hydroxy-propylmethyl-cellulose: 1% | $10^{4.16}$ | $10^{3.79}$ |

| Batch n° | Fomulation composition | Viral titer at time = zero after lyophilisation | Viral titer after lyopjhilisation and 1 week at 37° |
|---|---|---|---|
| 00C24/05 | Sucrose: 2%<br>Dextran: 4%<br>Sorbitol: 3%<br>Am. Acids: 2%<br>CaCO₃: 60 mg<br>Xanthane 0.3% | $10^{5.02}$ | $10^{4.54}$ |
| 00C24/06 | Sucrose: 2%<br>Dextran: 4%<br>Sorbitol: 3%<br>Am. Acids: 2%<br>CaCO₃: 60 mg<br>Xanthane 0.3% | $10^{4.86}$ | $10^{4.56}$ |
| 00F26/11 | Sucrose: 1%<br>Dextran: 2%<br>Sorbitol: 1.5%<br>Am. Acids: 1%<br>CaCO₃: 60 mg<br>Starch: 2% | $10^{4.70}$ | $10^{4.40}$ |

In the "lyoc concept" both Xanthane and Starch can be used (maintaining the quick dissolution properties of the lyophilised cake).

Example 6

Use of Calcium Carbonate as the Antacid for the Rotavirus vaccine Composition

When a suspension of CaCO₃ in water is used as the antacid for Rotavirus there is a problem that the calcium carbonate particles sediment rapidly when placed in water since the powder density value approaches 2.6 and the average particle size is 30 μm.

This sedimentation can be slowed by:
1 increasing the density of the surrounding medium
2 increasing the viscosity of the surrounding medium
3 reducing the particles size
4 keeping particles away from each other 6.1: Increasing Density of the Surrounding Medium:

When the CaCO₃-Water suspension (when placed in the syringe) is placed on the lyophilised cake (containing sucrose 2%, dextran 4%; sorbitol 3%; amino-acids 2%) the density of the surrounding medium is increased, but the speed of CaCO₃ sedimentation is not very much different from the CaCO₃-Water suspension.

6.2 Increasing the Viscosity of the Surrounding Medium:

Pseudoplastic Excipents

A pseudoplastic solution is defined as a solution having higher viscosity on standing compared to its viscosity under agitation.

Usual excipients of this type are:
Natural Polymers for Example:
  arabic gum
  adragante gum
  agar-agar
  alginates
  pectines
Semi-Synthetic Polymers for Example:
  carboxymethylcellulose (Tyloses C©)
  methylcellulose (Methocels A®, Viscotrans MC®, Tylose MH® and MB®)
  hydroxypropylcellulose (Klucels®)
  hydroxypropylmethylcellulose (Methocels E® and K®, Viscontrans MPHC®)
In general those pseudoplastic excipients are used together with thixotropic agents.

Pseudoplastic Excipients with Low Flowing Capacity
Those polymers, at a sufficient concentration, give rise to a structural fluid arrangement resulting in a high viscosity solution having low flowing capacity on standing. A certain quantity of energy needs to be given to the system to allow flowing and transfer.

External energies (agitation) are needed to destroy temporarily the structural fluid arrangement in order to obtain a fluid solution.
Examples of such polymers are Carbopols® and Xanthane gum.
Thixotropic Excipents
With these excipents, on standing, a gel structure is obtained; while under agitation a fluid solution is obtained.

Examples of thixotropic excipients are: Veegum® (Magnesium-aluminium silicate) and Avicel RC® (about 89% microcrystalline cellulose and 11% Caboxymethylcellulose Na).

6.3 Reducing the Particles Size
A reduction in the $CaCO_3$ particle size resulted in a decrease in the antacid capacity of the compound.

6.4 Keeping Particles away from each Other
This is the case in Veegum® and Avicel® for which insoluble particles smaller (about 1 µm) than the $CaCO_3$ particles, are placed between $CaCO_3$ particles in order to prevent aggregation.

Example 7

Product Design

The following schemes demonstrate examples of possible product designs.

7.1 $CaCO_3$ in the Syringe
Having already clinical batches of Rotavirus in lyophilised vials, the antacid can be placed in the reconstituent liquid contained in the syringe.
In this product presentation, sedimentation of $CaCO_3$ must be under control not only during the filling steps, but also during the complete shelf-live of the product (at least 2 years).

7.2 $CaCO_3$ in the Lyophilised Vial 7.3. Lyophilisation in a Blister
In this case Rotavirus, $CaCO_3$ and Xanthane gum are lyophilised together directly in the blister.

Example 8

Lyophilisation of Different Strain of Rotavirus

| Batch n° | Rotavirus strain | Fomulation composition | Viral titer at t = zero after lyophilisation | Viral titer after lyopjhilisation and 1 week at 37° |
|---|---|---|---|---|
| 00F26/01 | G1 SB purif n°61 PRO/0232 | Sucrose: 2% Dextran: 4% Sorbitol: 3% Am. Acids: 2% | $10^{4.6}$ | $10^{4.7}$ |
| 00F26/02 | G2 (DS-1) | Sucrose: 2% Dextran: 4% Sorbitol: 3% Am. Acids: 2% | $10^{4.4}$ | $10^{4.4}$ |
| 00F26/03 | G3(P) | Sucrose: 2% Dextran: 4% Sorbitol: 3% Am. Acids: 2% | $10^{4.6}$ | $10^{4.5}$ |
| 00F26/04 | G4 (VA-70) | Sucrose: 2% Dextran: 4% Sorbitol: 3% Am. Acids: 2% | $10^{4.8}$ | $10^{4.8}$ |
| 00F26/05 | G9 (W161) | Sucrose: 2% Dextran: 4% Sorbitol: 3% Am. Acids: 2% | $10^{4.6}$ | $10^{4.5}$ |

The strains DS-1, P and VA70 are described as Human rotavirus reference strains for serotype G2, G3 and G4 respectively at page 1361 of "Fields" Raven press 1990, second edition.
In this experiment different Rotavirus strains have been lyophilised.
For all, both the viral titer have been maintained during lyophilisation and accelarated stability (one week at 37° C.) has been shown.

Example 9

Phase I Safety Study in Adults of One Oral Administration of the Rotavirus Vaccine A Phase I study was carried out to assess the safety and reactogenicity of a single oral dose of $10^{6.0}$ ffu of the P43 vaccine in healthy adults aged 18 to 45 years.

The clinical trial was double blind and randomized. It was placebo-controlled and self-contained. The study was performed in one single centre in Belgium.

Study Population

A total of 33 subjects, 11 in the placebo group and 22 in the vaccine group, were enrolled and all completed the study. All volunteers were Caucasians. Their mean age at the time of vaccination was 35.3 years, with a range of 18 to 44 years. The trial began in January and ran for just over one month.

Material

Vaccine

Clinical lots of P43 vaccine were produced, purified, formulated and lyophilized according to Good Manufacturing Practices. The lots were released by Quality Control and Quality Assurance. Each vial of vaccine contained the following components:

| Active ingredient: | |
| --- | --- |
| P43 strain | Min. $10^{5.8}$ ffu |

| Excipients, stabilizers: | |
| --- | --- |
| Sucrose | 9 mg |
| Dextran | 18 mg |
| Sorbitol | 13.5 mg |
| Amino acids | 9 mg |

Placebo

Vials of placebo were prepared and released. Each vial of placebo contained the following components:

| Excipients, stabilizers: | |
| --- | --- |
| Sucrose | 9 mg |
| Dextran | 18 mg |
| Sorbitol | 13.5 mg |
| Amino acids | 9 mg |

Diluent

Water for injection was used as diluent to reconstitute vaccine and placebo.

Administration

Approximately 10 to 15 minutes before administration of the vaccine or the placebo, subjects of both groups were given 10 ml of Mylanta® orally. Mylanta® is a registered antacid. The antacid increases the pH of the stomach and prevents inactivation of the rotavirus during its passage through the stomach.

To prepare the vaccine, two vials of lyophilized P43 containing $10^{5.8}$ ffu per vial were reconstituted with 1.5 ml of diluent water for injection. This achieved a calculated viral titer of $10^{6.1}$ ffu per dose. The reconstituted vaccine was administered promptly as a single oral dose.

To prepare the placebo, two vials of lyophilized placebo were reconstituted with 1.5 ml water for injection and administered orally as a single dose.

Safety and Reactogenicity

The following criteria of safety and reactogenicity applied:

Solicited general symptoms were fever, diarrhea, vomiting, nausea, abdominal pain and loss of appetite. They were recorded during eight days post administration.

Unsolicited symptoms were recorded during 30 days post administration.

Serious adverse events were recorded during the entire study period.

Diarrhea samples were to be collected during eight days post administration.

The results were:

No solicited symptoms, no unsolicited and no serious adverse events were reported during the respective observation periods.

No cases of diarrhea were reported.

CONCLUSIONS

SB Biologicals P43 vaccine was safe relative to the placebo when administered orally in a double-blind fashion as a single dose at the dose of $10^{6.1}$ ffu to healthy adult volunteers aged 18 to 44.

---

The invention claimed is:

1. A homogeneous attenuated human rotavirus population comprising a single variant or substantially a single variant comprising less than 1% of a different variant, which variant is defined by a polypeptide sequence of:
- a VP4 protein comprising at least one of a phenylalanine (Phe) at position 167, a glutamic acid (Glu) at position 263, and an arginine (Arg) at position 268;
and,
- a VP7 protein comprising at least one of a methionine (Met) at position 202, and an isoleucine (Ile) at position 299.

2. The rotavirus population of claim 1, wherein the rotavirus population is a cloned strain.

3. The rotavirus population of claim 1, wherein the rotavirus population is derived from a human rotavirus infection.

4. The rotavirus population of claim 1, wherein the rotavirus population replicates in and is excreted by humans.

5. The rotavirus population of claim 1, wherein the substantially single variant is defined by a polypeptide sequence of:
- a VP4 protein comprising a phenylalanine (Phe) at position 167, a glutamic acid (Glu) at position 263, and an arginine (Arg) at position 268;
and,
- a VP7 protein comprising a methionine (Met) at position 202, and an isoleucine (Ile) at position 299.

6. The rotavirus population of claim 1, wherein the nucleotide sequence encoding VP4 comprises at least one of: an adenine base (A) at position 788; an adenine base (A) at position 802; and a thymine base (T) at position 501.

7. The rotavirus population of claim 6, wherein the nucleotide sequence encoding VP4 comprises an adenine base (A) at position 788; an adenine base (A) at position 802; and a thymine base (T) at position 501.

8. The rotavirus population of claim 7, wherein the nucleotide sequence encoding VP4 comprises the nucleotide sequence set forth in SEQ ID NO:1.

9. The rotavirus population of claim 1, wherein the nucleotide sequence encoding VP7 comprises at least one of: a thymine (T) at position 605; an adenine (A) at position 897; and a guanine (G) at position 897.

10. The rotavirus population of claim 9, wherein the nucleotide sequence encoding VP7 comprises a thymine (T) at position 605; an adenine (A) at position 897; and a guanine (G) at position 897.

11. The rotavirus population of claim 10, wherein the nucleotide sequence encoding VP7 comprises the nucleotide sequence set forth in SEQ ID NO:2.

12. The rotavirus population of claim 1, comprising the nucleotide sequence set forth in SEQ ID NO:1 and a nucleotide sequence encoding VP7.

13. The rotavirus population of claim 1, wherein the nucleotide sequence encoding VP4 comprises the nucleotide sequence set forth in SEQ ID NO:1 and the nucleotide sequence encoding VP7 comprises the nucleotide sequence set forth in SEQ ID NO:2.

14. The rotavirus population of claim 1, designated as P43 and deposited under accession number ECACC 99081301 and immunologically active progeny thereof.

15. A rotavirus reassortant comprising at least one antigen or at least one segment of the rotavirus variant P43 of claim 14.

16. A method of manufacturing a rotavirus vaccine comprising admixing the attenuated human rotavirus population of claim 1 with an antacid and a viscous agent.

* * * * *

SEQUENCE LISTING

<160> NUMBER OF SEQ ID NOS: 34

<210> SEQ ID NO 1
<211> LENGTH: 2350
<212> TYPE: DNA
<213> ORGANISM: Homo sapien

<400> SEQUENCE: 1

```
atggcttcac tcatttatag acaacttctc actaattcat attcagtaga tttacatgat      60
gaaatagagc aaattggatc agaaaaaact cagaatgtaa ctataaatcc gggtccattt     120
```

```
gcacagacta gatatgctcc agtcaattgg gatcatggag agataaatga ttcgactaca    180
gtagaaccaa ttttagatgg tccttatcag ccaactacat ttactccacc taatgattat    240
tggatactta ttaattcaaa tacaaatgga gtagtatatg aaagtacaaa taatagtgac    300
ttttggactg cagtcgttgc tattgaaccg cacgtcaacc cagtagatag acaatatatg    360
atatttggtg aaagcaagca atttaatgtg agtaacgatt caaataaatg gaagttttta    420
gaaatgttta gaagcagtag tcaaaatgaa ttttataata gacgtacatt aacttctgat    480
accagacttg taggaatatt taaatatggt ggaagagtat ggacatttca tggtgaaaca    540
ccgagagcta ctactgacag ttcaagtact gcaaatttaa ataatatatc aattacaatt    600
cattcagaat tttacattat tccaaggtcc caggaatcta aatgtaatga atatattaat    660
aatggtctgc caccaattca aaatactaga aatgtagttc cattgccatt atcatctaga    720
tcgatacagt ataagagagc acaagttaat gaagacatta tagtttcaaa aacttcatta    780
tggaaagaaa tgcagtataa tagggatatt ataattagat ttaaatttgg taatagtatt    840
gtaaagatgg gaggactagg ttataaatgg tctgaaatat catataaggc agcaaaattat   900
caatataatt acttacgtga cggtgaacaa gtaaccgcac acaccacttg ttcagtaaat    960
ggagtgaaca attttagcta taatggaggg tttctaccca ctgattttgg tatttcaagg   1020
tatgaagtta ttaaagagaa ttcttatgta tatgtagact attgggatga ttcaaaagca   1080
tttagaaata tggtatatgt tagatcatta gcagctaatt taaattcagt gaaatgtaca   1140
ggtggaagtt attatttcag tataccagta ggtgcatggc cagtaatgaa tggtggcgct   1200
gtttcgttgc attttgccgg agttacatta tccacgcaat ttactgattt tgtatcatta   1260
aattcactac gatttagatt tagtttgaca gttgatgaac caccttttctc aatactgaga   1320
acacgtacag tgaatttgta tggattacca gccgctaatc caaataatgg aaatgaatac   1380
tacgaaatat caggaaggtt ttcactcatt tctttagttc caactaatga tgattatcag   1440
actccaatta tgaattcagt gacggtaaga caagatttag agcgccaact tactgattta   1500
cgagaagaat ttaactcatt gtcacaagaa atagctatgg cacaattgat tgatttagca   1560
ctgttgcctc tagatatgtt ttccatgttt tcaggaatta aaagtacaat tgatttaact   1620
aaatcaatgg cgactagtgt aatgaagaaa tttagaaaat caaaattagc tacatcaatt   1680
tcagaaatga ctaattcatt gtcagatgct gcttcatcag catcaagaaa cgtttctatt   1740
agatcgaatt tatctgcgat ttcaaattgg actaatgttt caaatgatgt gtcaaacgta   1800
actaattcat tgaacgatat ttcaacacaa acatctacaa ttagtaagaa acttagatta   1860
aaagaaatga ttactcaaac tgaaggaatg agctttgacg acatttcagc agctgtacta   1920
aaaacaaaaa tagatatgtc tactcaaatt ggaaaaaata ctttacctga tatagttaca   1980
gaagcatctg agaaatttat tccaaaacga tcatatcgaa tattaaagga tgatgaagta   2040
atggaaatta atactgaagg aaaattcttt gcatacaaaa ttaatacatt tgatgaagtg   2100
ccattcgatg taaataaatt cgctgaacta gtaacagatt ctccagttat atcagcgata   2160
atcgatttta agacattgaa aaatttaaat gataattatg gaatcactcg tacagaagcg   2220
ttaaattta ttaaatcgaa tccaaatatg ttacgtaatt tcattaatca aaataatcca   2280
attataagga atagaattga acagttaata ctacaatgta aattgtgaga acgctattga   2340
ggatgtgacc                                                          2350
```

<210> SEQ ID NO 2

<211> LENGTH: 1009
<212> TYPE: DNA
<213> ORGANISM: Homo sapien

<400> SEQUENCE: 2

| | | | | | |
|---|---|---|---|---|---|
| atgtatggtc | ttgaatatac | cacaattcta | atctttctga | tatcaattat | tctactcaac | 60 |
| tatatattaa | aatcagtaac | tcgaataatg | gactacatta | tatatagatc | tttgttgatt | 120 |
| tatgtagcat | tatttgcctt | gacaagagct | cagaattatg | ggcttaactt | accaataaca | 180 |
| ggatcaatgg | acactgtata | cgctaactct | actcaagaag | gaatatttct | aacatccaca | 240 |
| ttatgtttgt | attatccaac | tgaagcaagt | actcaaatta | tgatggtga | atggaaagac | 300 |
| tcattgtcac | aaatgtttct | cacaaaaggt | tggccaacag | gatcagtcta | ttttaaagag | 360 |
| tattcaagta | ttgttgattt | ttctgtcgat | ccacaattat | attgtgatta | taacttagta | 420 |
| ctaatgaaat | atgatcaaaa | tcttgaatta | gatatgtcag | agttagctga | tttaatattg | 480 |
| aatgaatggt | tatgtaatcc | aatggatata | acattatatt | attatcaaca | atcgggagaa | 540 |
| tcaaataagt | ggatatcaat | gggatcatca | tgtactgtga | aagtgtgtcc | actgaatacg | 600 |
| caaatgttag | gaataggttg | tcaaacaaca | aatgtagact | cgtttgaaat | ggttgctgag | 660 |
| aatgagaaat | tagctatagt | ggatgtcgtt | gatgggataa | atcataaaat | aaatttgaca | 720 |
| actacgacat | gtactattcg | aaattgtaag | aagttaggtc | caagagagaa | tgtagctgta | 780 |
| atacaagttg | gtggctctaa | tgtattagac | ataacagcag | atccaacgac | taatccacaa | 840 |
| actgagagaa | tgatgagagt | gaattggaaa | aaatggtggc | aagtatttta | tactatagta | 900 |
| gattatatta | accaaatcgt | gcaggtaatg | tccaaaagat | caagatcatt | aaattctgca | 960 |
| gcttttatt | atagagtata | gatatatctt | agattagatc | gatgtgacc | | 1009 |

<210> SEQ ID NO 3
<211> LENGTH: 28
<212> TYPE: DNA
<213> ORGANISM: Artificial Sequence
<220> FEATURE:
<223> OTHER INFORMATION: Oligonucleotide

<400> SEQUENCE: 3
ggctttaaaa gagagaattt ccgtctgg                                      28

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide

<400> SEQUENCE: 4
ggttagctcc ttttaatgta tggta                                         25

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide

<400> SEQUENCE: 5
ggtcacatcg aacaattcta atctaag                                       27

<210> SEQ ID NO 6
<211> LENGTH: 22

```
<212> TYPE: DNA
<213> ORGANISM: Artificial Sequence
<220> FEATURE:
<223> OTHER INFORMATION: Oligonucleotide

<400> SEQUENCE: 6
caagtactca aatcaatgat gg                                           22

<210> SEQ ID NO 7
<211> LENGTH: 23
<212> TYPE: DNA
<213> ORGANISM: Artificial Sequence
<220> FEATURE:
<223> OTHER INFORMATION: Oligonucleotide

<400> SEQUENCE: 7
tgttgatttt tctgtcgatc cac                                          23

<210> SEQ ID NO 8
<211> LENGTH: 32
<212> TYPE: DNA
<213> ORGANISM: Artificial Sequence
<220> FEATURE:
<223> OTHER INFORMATION: Oligonucleotide

<400> SEQUENCE: 8
ggttgctgag aatgagaaat tagctatagt gg                                32

<210> SEQ ID NO 9
<211> LENGTH: 32
<212> TYPE: DNA
<213> ORGANISM: Artificial Sequence
<220> FEATURE:
<223> OTHER INFORMATION: Oligonucleotide

<400> SEQUENCE: 9
ccactatagc taatttctca ttctcagcaa cc                                32

<210> SEQ ID NO 10
<211> LENGTH: 22
<212> TYPE: DNA
<213> ORGANISM: Artificial Sequence
<220> FEATURE:
<223> OTHER INFORMATION: Oligonucleotide

<400> SEQUENCE: 10
tggcttcgcc attttataga ca                                           22

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
atttcggacc atttataacc                                              20

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide

<400> SEQUENCE: 12
```

-continued

| | |
|---|---|
| tggcttcact catttataga ca | 22 |

<210> SEQ ID NO 13
<211> LENGTH: 23
<212> TYPE: DNA
<213> ORGANISM: Artificial Sequence
<220> FEATURE:
<223> OTHER INFORMATION: Oligonucleotide

<400> SEQUENCE: 13

| | |
|---|---|
| atttcagacc atttataacc tag | 23 |

<210> SEQ ID NO 14
<211> LENGTH: 29
<212> TYPE: DNA
<213> ORGANISM: Artificial Sequence
<220> FEATURE:
<223> OTHER INFORMATION: Oligonucleotide

<400> SEQUENCE: 14

| | |
|---|---|
| ggagtagtat atgaaagtac aaataatag | 29 |

<210> SEQ ID NO 15
<211> LENGTH: 29
<212> TYPE: DNA
<213> ORGANISM: Artificial Sequence
<220> FEATURE:
<223> OTHER INFORMATION: Oligonucleotide

<400> SEQUENCE: 15

| | |
|---|---|
| ctattatttg tactttcata tactactcc | 29 |

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide

<400> SEQUENCE: 16

| | |
|---|---|
| tcgatacagt ataagagagc acaag | 25 |

<210> SEQ ID NO 17
<211> LENGTH: 27
<212> TYPE: DNA
<213> ORGANISM: Artificial Sequence
<220> FEATURE:
<223> OTHER INFORMATION: Oligonucleotide

<400> SEQUENCE: 17

| | |
|---|---|
| ttcattaact tgtgctctct tatactg | 27 |

<210> SEQ ID NO 18
<211> LENGTH: 22
<212> TYPE: DNA
<213> ORGANISM: Artificial Sequence
<220> FEATURE:
<223> OTHER INFORMATION: Oligonucleotide

<400> SEQUENCE: 18

| | |
|---|---|
| gtatatgtag actattggga tg | 22 |

<210> SEQ ID NO 19
<211> LENGTH: 22
<212> TYPE: DNA
<213> ORGANISM: Artificial Sequence

```
<220> FEATURE:
<223> OTHER INFORMATION: Oligonucleotide

<400> SEQUENCE: 19
catcccaata gtctacatat ac                                              22

<210> SEQ ID NO 20
<211> LENGTH: 23
<212> TYPE: DNA
<213> ORGANISM: Artificial Sequence
<220> FEATURE:
<223> OTHER INFORMATION: Oligonucleotide

<400> SEQUENCE: 20
tgtaactccg gcaaaatgca acg                                             23

<210> SEQ ID NO 21
<211> LENGTH: 23
<212> TYPE: DNA
<213> ORGANISM: Artificial Sequence
<220> FEATURE:
<223> OTHER INFORMATION: Oligonucleotide

<400> SEQUENCE: 21
cgttgcattt tgccggagtt aca                                             23

<210> SEQ ID NO 22
<211> LENGTH: 23
<212> TYPE: DNA
<213> ORGANISM: Artificial Sequence
<220> FEATURE:
<223> OTHER INFORMATION: Oligonucleotide

<400> SEQUENCE: 22
gtaagacaag atttagagcg cca                                             23

<210> SEQ ID NO 23
<211> LENGTH: 23
<212> TYPE: DNA
<213> ORGANISM: Artificial Sequence
<220> FEATURE:
<223> OTHER INFORMATION: Oligonucleotide

<400> SEQUENCE: 23
tggcgctcta aatcttgtct tac                                             23

<210> SEQ ID NO 24
<211> LENGTH: 25
<212> TYPE: DNA
<213> ORGANISM: Artificial Sequence
<220> FEATURE:
<223> OTHER INFORMATION: Oligonucleotide

<400> SEQUENCE: 24
cttgatgctg atgaagcagc atctg                                           25

<210> SEQ ID NO 25
<211> LENGTH: 25
<212> TYPE: DNA
<213> ORGANISM: Artificial Sequence
<220> FEATURE:
<223> OTHER INFORMATION: Oligonucleotide

<400> SEQUENCE: 25
cagatgctgc ttcatcagca tcaag                                           25
```

<210> SEQ ID NO 26
<211> LENGTH: 25
<212> TYPE: DNA
<213> ORGANISM: Artificial Sequence
<220> FEATURE:
<223> OTHER INFORMATION: Oligonucleotide

<400> SEQUENCE: 26
cgatcatatc gaatattaaa ggatg                                    25

<210> SEQ ID NO 27
<211> LENGTH: 25
<212> TYPE: DNA
<213> ORGANISM: Artificial Sequence
<220> FEATURE:
<223> OTHER INFORMATION: Oligonucleotide

<400> SEQUENCE: 27
catcctttaa tattcgatat gatcg                                    25

<210> SEQ ID NO 28
<211> LENGTH: 25
<212> TYPE: DNA
<213> ORGANISM: Artificial Sequence
<220> FEATURE:
<223> OTHER INFORMATION: Oligonucleotide

<400> SEQUENCE: 28
agcgttcaca caatttacat tgtag                                    25

<210> SEQ ID NO 29
<211> LENGTH: 32
<212> TYPE: DNA
<213> ORGANISM: Artificial Sequence
<220> FEATURE:
<223> OTHER INFORMATION: Oligonucleotide

<400> SEQUENCE: 29
agtattttat actatagtag attatattaa tc                            32

<210> SEQ ID NO 30
<211> LENGTH: 32
<212> TYPE: DNA
<213> ORGANISM: Artificial Sequence
<220> FEATURE:
<223> OTHER INFORMATION: Oligonucleotide

<400> SEQUENCE: 30
agtattttat actatggtag attatattaa tc                            32

<210> SEQ ID NO 31
<211> LENGTH: 25
<212> TYPE: DNA
<213> ORGANISM: Artificial Sequence
<220> FEATURE:
<223> OTHER INFORMATION: Oligonucleotide

<400> SEQUENCE: 31
atccccatta tactgcattc ctttc                                    25

<210> SEQ ID NO 32
<211> LENGTH: 25
<212> TYPE: DNA
<213> ORGANISM: Artificial Sequence
<220> FEATURE:
<223> OTHER INFORMATION: Oligonucleotide

```
<400> SEQUENCE: 32
atccctatta tactgcattt ctttc                                         25

<210> SEQ ID NO 33
<211> LENGTH: 25
<212> TYPE: DNA
<213> ORGANISM: Artificial Sequence
<220> FEATURE:
<223> OTHER INFORMATION: Oligonucleotide

<400> SEQUENCE: 33 atcccccatta tactgcattt ctttc                                        25

<210> SEQ ID NO 34
<211> LENGTH: 25
<212> TYPE: DNA
<213> ORGANISM: Artificial Sequence
<220> FEATURE:
<223> OTHER INFORMATION: Oligonucleotide

<400> SEQUENCE: 34
atccctatta tactgcattc ctttc                                         25
```